United States Patent
Fernandez et al.

(10) Patent No.: US 9,384,323 B1
(45) Date of Patent: *Jul. 5, 2016

(54) PHARMACO-GENOMIC MUTATION LABELING

(76) Inventors: Dennis S. Fernandez, Atherton, CA (US); Antonia Teresita Ancheta Maninang, Atherton, CA (US)

(*) Notice: Subject to any disclaimer, the term of this patent is extended or adjusted under 35 U.S.C. 154(b) by 1079 days.

This patent is subject to a terminal disclaimer.

(21) Appl. No.: 12/351,552

(22) Filed: Jan. 9, 2009

Related U.S. Application Data

(62) Division of application No. 10/277,213, filed on Oct. 18, 2002, now abandoned.

(51) Int. Cl.
*G01N 33/48* (2006.01)
*G06F 19/00* (2011.01)

(52) U.S. Cl.
CPC .................................... *G06F 19/34* (2013.01)

(58) Field of Classification Search
CPC ....................................................... G06F 19/34
USPC ............................................................ 702/19
See application file for complete search history.

(56) References Cited

U.S. PATENT DOCUMENTS

| | | | |
|---|---|---|---|
| 5,076,271 A | 12/1991 | Lekholm et al. | |
| 5,328,847 A | 7/1994 | Case et al. | |
| 5,390,238 A | 2/1995 | Kirk et al. | |
| 5,441,047 A | 8/1995 | David et al. | |
| 5,594,638 A | 1/1997 | Iliff | |
| 5,632,041 A | 5/1997 | Peterson et al. | |
| 5,672,686 A | 9/1997 | Chittenden | |
| 5,706,498 A | 1/1998 | Fujimiya et al. | |
| 5,736,342 A | 4/1998 | Van Wie et al. | |
| 5,764,923 A | 6/1998 | Tallman et al. | |
| 5,774,357 A | 6/1998 | Hoffberg et al. | |
| 5,784,635 A | 7/1998 | McCallum | |
| 5,810,735 A | 9/1998 | Halperin et al. | |
| 5,822,544 A | 10/1998 | Chaco et al. | |
| 5,837,832 A | 11/1998 | Chee et al. | |
| 5,856,174 A | 1/1999 | Lipshutz et al. | |
| 5,874,219 A | 2/1999 | Rava et al. | |
| 5,876,926 A | 3/1999 | Beecham | |
| 5,968,755 A | 10/1999 | Roederer et al. | |
| 5,994,075 A | 11/1999 | Goodfellow | |
| 6,042,548 A | 3/2000 | Gluffre et al. | |
| 6,064,754 A | 5/2000 | Parekh et al. | |
| 6,112,116 A | 8/2000 | Fischell et al. | |
| 6,122,536 A | 9/2000 | Sun et al. | |
| 6,168,948 B1 | 1/2001 | Anderson et al. | |
| 6,178,349 B1 | 1/2001 | Kleval | |
| 6,197,595 B1 | 3/2001 | Anderson et al. | |
| 6,207,392 B1 | 3/2001 | Weiss et al. | |
| 6,221,585 B1 | 4/2001 | Iris et al. | |
| 6,246,975 B1 | 6/2001 | Rivonelli et al. | |
| 6,272,379 B1 | 8/2001 | Fischell et al. | |
| 6,278,794 B1 | 8/2001 | Parekh et al. | |
| 6,285,897 B1 | 9/2001 | Kilcoyne et al. | |
| 6,291,182 B1 | 9/2001 | Schork et al. | |
| 6,300,141 B1 * | 10/2001 | Segal et al. ................. 435/287.1 | |
| 6,315,720 B1 | 11/2001 | Williams et al. | |
| 6,317,719 B1 | 11/2001 | Schrier et al. | |
| 6,358,202 B1 | 3/2002 | Arent | |
| 6,379,971 B1 | 4/2002 | Schneider et al. | |
| 6,381,025 B1 | 4/2002 | Bornhop et al. | |
| 6,389,428 B1 | 5/2002 | Rigault et al. | |
| 6,395,480 B1 | 5/2002 | Hefti | |
| 6,399,365 B2 | 6/2002 | Besemer | |
| 6,402,689 B1 | 6/2002 | Scarantino et al. | |
| 6,409,674 B1 | 6/2002 | Brockway et al. | |
| 6,423,001 B1 | 7/2002 | Abreu et al. | |
| 6,428,951 B1 | 8/2002 | Michnick et al. | |
| 6,428,964 B1 | 8/2002 | Shuber | |
| 6,432,050 B1 | 8/2002 | Porat et al. | |
| 6,454,708 B1 | 9/2002 | Ferguson et al. | |
| 6,458,086 B1 | 10/2002 | Franco et al. | |
| 6,475,750 B1 | 11/2002 | Han et al. | |
| 6,486,588 B2 | 11/2002 | Doron et al. | |
| 6,490,030 B1 | 12/2002 | Gill et al. | |
| 6,514,689 B2 | 2/2003 | Han et al. | |
| 6,542,858 B1 | 4/2003 | Grass et al. | |
| 6,544,193 B2 | 4/2003 | Abreu et al. | |
| 6,546,268 B1 | 4/2003 | Ishikawa et al. | |
| 6,546,269 B1 | 4/2003 | Kurnik | |
| 6,551,838 B2 | 4/2003 | Santini, Jr. et al. | |
| 6,553,244 B2 | 4/2003 | Lesho et al. | |
| 6,558,957 B1 | 5/2003 | Rolnestad et al. | |

(Continued)

FOREIGN PATENT DOCUMENTS

| EP | 0867830 A2 | 9/1998 |
|---|---|---|
| EP | 1318472 | 6/2003 |

(Continued)

OTHER PUBLICATIONS

Warren et al., "VCSEL Applications in Sensors and Microsystems," SPIE (1998) vol. 3286, pp. 42-51.*
Schmidt et al., "Protein Sequence Comparison on the Instruction Systolic Array," LNCS (2001) vol. 2127/2001, pp. 498-509.*
Saffo, Paul, Sensors: The Next Wave of Infotech Innovation. Institute for the Future, 1997. p. 115-122.
Mechkour, M. et al., Prime-GC, "A Medical Information Retrival Prototype on the Web," 1997, IEEE, BP 53 38041, Grenoble Cedex 9, France.
Grigsby et al., "Telemedicine: where it is and where it's going," 1998 Annals of Internal Medicine.1998. vol. 129(2) p. 123-126.
Executive Summary 1998, Institute for the future. Health Care Horizons Report.1998 p. 1-6.
Ganguly, Pronab et al., Telemedicine over enterprise—wide networks: a case study, 1998 IEEE, p. 1297-1302.
Pavlopoulos, S. et al., Design and Development of a web-based hospital information system, IEEE 1998, p. 1188-1191.
Long, R. et al. "Understanding Individual Variations in Drug Responses: from Phenotype to Genotype." NIGMS (online) 1998 (Retrived on Jun. 27, 2002) Retrived from the Internet:<URL:http://nigms.nih.gov/news/reports/pharmacogenetics.html>.
"Pharmacogenetics in Patient Care." AACC (online)1998. (Retrived on Jul. 20, 2002) Retrived from the Internet: <URL:http//www.aacc.org/pharmacogenetics/>.

(Continued)

*Primary Examiner* — Jerry Lin
(74) *Attorney, Agent, or Firm* — Fernandez & Associates, LLP

(57) ABSTRACT

Electronic label processor compares bioinformatic values to determine pharmaco-genomic mutation associated with host. Label display indicates pharmaco-genomic mutation, which is network-accessible for modified medical message. Bioinformatic values are determined preferably at different times.

10 Claims, 1 Drawing Sheet

(56) References Cited

U.S. PATENT DOCUMENTS

| | | | |
|---|---|---|---|
| 6,561,978 | B1 | 5/2003 | Conn et al. |
| 6,575,912 | B1 | 6/2003 | Turcott |
| 6,610,489 | B2 | 8/2003 | Wolffe et al. |
| 6,887,714 | B2 | 5/2005 | Fritsch et al. |
| 6,970,741 | B1 | 11/2005 | Whitehurst et al. |
| 6,994,245 | B2 | 2/2006 | Pinchot |
| 7,147,441 | B2 | 12/2006 | Fritsch et al. |
| 7,467,928 | B2 | 12/2008 | Fakunle et al. |
| 7,542,959 | B2 | 6/2009 | Barnhill et al. |
| 7,563,882 | B2 | 7/2009 | Zauderer et al. |
| 7,750,125 | B2 | 7/2010 | Zauderer et al. |
| 2001/0023078 | A1 | 9/2001 | Bawendi et al. |
| 2001/0034034 | A1 | 10/2001 | Bruchez et al. |
| 2002/0019022 | A1 | 2/2002 | Dunn et al. |
| 2002/0127561 | A1 | 9/2002 | Bee et al. |
| 2002/0133495 | A1 | 9/2002 | Rienhoff, Jr. |
| 2002/0151816 | A1 | 10/2002 | Rich et al. |
| 2002/0197632 | A1 | 12/2002 | Moskowitz |
| 2003/0008407 | A1 | 1/2003 | Fu |
| 2003/0023388 | A1 | 1/2003 | Wagner |
| 2003/0027223 | A1 | 2/2003 | Muraca |
| 2003/0033168 | A1 | 2/2003 | Califano et al. |
| 2003/0060726 | A1 | 3/2003 | Lin et al. |
| 2003/0188326 | A1 | 10/2003 | D'Andrea et al. |
| 2004/0006433 | A1 | 1/2004 | Robson et al. |
| 2004/0030503 | A1 | 2/2004 | Arouh et al. |
| 2004/0088116 | A1 | 5/2004 | Khalil et al. |
| 2005/0101841 | A9 | 5/2005 | Kaylor et al. |
| 2008/0299094 | A1 | 12/2008 | Oren |

FOREIGN PATENT DOCUMENTS

| | | |
|---|---|---|
| EP | 1-246-114 A3 | 7/2004 |
| EP | 1507216 | 2/2005 |
| GB | 2325760 A | 12/1998 |
| GB | 2405203 B | 8/2004 |
| GB | 2441078 A | 11/2007 |
| WO | WO-94/00818 A1 | 1/1994 |
| WO | 9622574 | 7/1996 |
| WO | WO-97/09678 A1 | 3/1997 |
| WO | WO 97/27560 A1 | 7/1997 |
| WO | WO 98/35609 | 8/1998 |
| WO | WO 00/28893 A1 | 5/2000 |
| WO | WO-00/43552 A3 | 7/2000 |
| WO | 0169244 | 9/2001 |
| WO | WO-01/78652 A3 | 10/2001 |
| WO | WO-02/06266 A1 | 1/2002 |
| WO | WO-02/09119 A2 | 1/2002 |
| WO | WO-02/24862 A3 | 3/2002 |
| WO | WO 02/25528 A1 | 3/2002 |
| WO | 02065119 | 8/2002 |
| WO | 02091119 | 11/2002 |
| WO | WO-02/091119 | 11/2002 |
| WO | 02103608 | 12/2002 |
| WO | WO-03/05628 A3 | 1/2003 |
| WO | WO-03/17177 A3 | 2/2003 |
| WO | WO-03/43684 A1 | 5/2003 |
| WO | 03077062 | 9/2003 |
| WO | 2004047020 | 6/2004 |

OTHER PUBLICATIONS

Ferratt, Thomas et al.,Surmounting Health Information Network Barriers;the Greater dayton area experience. Health Care Management 1998 p. 70-76 (Aspen Publishers, Boston).

"What is Pharmacogenetics?"Impact (online). Jun. 1999 (Retrived on Jun. 27, 2002). Retrived from the Internet: <http://www.uscf.edu/foundation/impact/archives/1999/17-pharmacog.html.

Atalay, Besin et al. HIVPCES: A www-based HIV Patient Care Expert System, IEEE. 1999 p. 214-219.

Baker, Dixie et al. A design for secure communication of personal health information via the internet. Medical Informatics 1999 vol. 54 p. 97-104 (Elsevier, Amsterdam).

Malamateniou, F. et al., A search engine for virtual patient records. Medical Informatics.1999 vol. 55 p. 103-115. (Elsevier, Amsterdam).

Aizawa, Masuo et al. Protein Engineering for Biosensors.Protein Engineering in Industrial Biotechnology, p. 246-265. (Harwood academic Publishers, 2000 Itlay).

Mendible, Juan C., "Pharmacogenomics: Medicines Tailored Just for You," (online) 2000. Retrived from the Internet:<URL:http://www.suite101.com/print article>.

Jing Kong, Nathan R. Franklin, Chongwu Zhou, Michael G. Chapline, Shu Peng, Kyeongjue Cho, Hongjer Dui, Jan. 28, 2000, "Nanotubel Molecular Wires as Chemcial Sensors" Science Mag. (online) 2000. (Retrived on Jun. 27, 2002). Retrived from the Internet: <URL:http://www.sciencemag.org>.

Davis, Alison. "NIH effort to Understand How Genes Affect People's Responses to Medicines."NIGMS (online) 2000. (Retrived on Jun. 27, 2002) Retrived from the Internet:<URL:http://www.nigms.nih.gov/news/releases/pharmacogenetics.html>.

Thompson, Cheryl. "NIH starts pharmacogenetics netowrk." American Society of Health System Pharmacists (online) 2000. (Retrived on Jul. 20, 2002) Retrived from the Internet: <URL:http://www.org.nigms.nih.gov/news/releases/pharmacogenetics.html>.

Lathrop, J. et al., "Health Cares New Electronic Marketplace." Strategy Business. 1999 vol. 19 p. 34-43.

Richards, Joy "Nursing in a Digital Age," Nursing Economics 2001 vol. 19(1) p. 6-34.

Hensley, Scott et al., "Next Milestone in Human Genetics," The Wall Street Journal, May 26, 2000 p. B1.

Gulcher, Jeffery et al.,, "The Icelandic Healthcare Database and Informed Consent," The New England Journal of Medicine, Jun. 2000 vol. 342(24) p. 1-5.

Idekker, Trey et al., "A New Approach to Decoding Life: Systems Biology," Annul. Rev. Genomics Hum. Gen. 2001 vol. 2 p. 343-72.

The Power of Pharmacogenetics: TPMT, DNA Sciences Laboratories. (online) 2002. Retrived from the Internet:<URL://www.DNASciences.com>.

Hollon, Tom. The making of the pharmacogenomic prescription. Geneletter (online) 2001. (Retrived on Jun. 27, 2002)Retrived from the Internet:<www.geneletter.com/01-02-01/features>.

Khoury, Muin et al., "Will genetics revolutionize medicine?" Geneletter(online) 2001. (Retrived on Jun. 27, 2002) Retrived from the Internet:< www.geneltter.com/01-02-01/features>.

Khoury, M. et al., "Pharmacogenomics & Public Health: The Promise of Targeted Disease Prevention." CDC(online)2001. (Retrived on Jun. 27, 2002) Retrived from the Internet:<www.cdc.gov/genomics/info/ factshts/html>.

Walsh, Barbara. "Genotyping for prescriptions underutilized." Geneletter(online) 2001. (Retrived on Jun. 27, 2002) Retrived from the Internet:<www.geneletter.com/01-02-01/letters>.

Lipp, Elizabeth. Pharmacogenomics Research & Methodologles.Genetic Engineering News. 2001 vol. 21(4) p. 21-26.

Davis, Alison et al. Pharmacogenetics Research Network & Knowledge Base.Pharmacogenomics 2001 vol. 2 (3) p. 285-289.

Pharmacogenomics: Findin the Competitive Edge in Genetic Variation, Cambridge Health Institute (online)2001 (Retrived on Jun. 27, 2002) Retrived from the Internet:.<URL:http://www.chireports.com/content/reports/toc/printpage.asp?R/pharmacogenomics01.toc. AS>.

"Pharmco-Genetics:Finding the right Medicine for Each Patient."DNA Sciences. (online)2002 (Retrived on Jul. 20, 2002)Retrived from the Internet:<http://www.ppgx.com>.

"Pharmacogenomics." Human genome Project Information. (online) 2002. (Retrived on Jun. 27, 2002)Retrived from the Internet(http://www.ornl.gov/hgmis/medicine/pharma.html>.

"The good of small things" Science and Technology (online)2001 .(Retrived on Jan. 11, 2002) Retrived from the Internet:<URL:http://www.economist.com>.

"Veri Chip" Datasheet from applied digital solutions corp. (online) 2001. (Retrived on Dec. 19, 2001) Retrived from the Internet:<URL:http://www.adsx.com/verichip/verichip.html>.

Johnson, Colin, "Smart Sensors Extend Web Scale," EE Times (online) 2001 (Retrived on May 1, 2001) Retrived from the Internet:<URL:http://www.eet.com/printable article?doc_id=>.

(56) References Cited

OTHER PUBLICATIONS

Sadee Wolfgang et al., "Genetic variations in human G-protein-coupled receptors: Implications for Drug Therapy." AAPS Pharmaceutica (online)2001 (Retrived on Jun. 27, 2002) Retrived from the Internet:<URL:http://www.pharmsci.org/scientifcjournals/pharmsci/journal/01-22.html>.
Aldridge, Susan "Customizing Drugs to Indivisual Genetic Profiles" Genetic Engineering News 2001. vol. 21 (14) p. 30.
"Genomics and its Impact on Medicine and Society" U.S. Department of Energy Human Genome Program, 2001. Produced by the Human Genome Management Information System p.1-12 primer. www.ornl.gov/hgmis.
"Categories of pharmacogenetic knowledge" Datasheet from pharmGKB (online) 2002 (Retrived on Jun. 27, 2002) Retrived from the Internet:<URL: http://servesessionid-24A5Etomcat?id>.
Love, Jennifer et al. Applications of Advances in Molecular Biology and Genomics to Clinical Cancer Care. Cancer Nursing 2002 vol. 25(2) p. 110-122.
"As the Science Succeeds, Patients Benefit" UCSF Center for Pharmacogenomics (online) 2002(Retrived on Jun. 27, 2002)Retrived from the Internet:<www.pharmacy.ucsf.edu/cpg/whatis/>.
"Technology forecasts" Batelle (online) 2002 (Retrived on Jul. 27, 2002) Retrived from the Internet:<URL:http://www.battle.org/forecasts/technology2020.stm>.
Scatimel, Bruno "Biosensors and Protepmics" vLifeScience (online)2002 (Retrived on Feb. 3, 2002) Retrived from the Internet:<URL:http://www.vLifeScience.com.au>.
Murray, Charles. Injectable chip opens door to 'human bar code'. EETIMES (online) 2002. (Retrived on Jan. 4, 2002) Retrived from the Internet:<www.eet.com/printablearticle?doc_id.
"IBM Mayo Clinic to collaborate on worldwide medical databse" SiliconValley.com (online) 2002 (Retrived on Mar. 25, 2002) Retrived from the Internet: <www.siliconvalley.com>.
Hamilton, David P. Custom Tailored Medicine. The Wall Street Journal Mar. 25, 2002 p. B1.
"Huge British gene bank gets $65 million go-ahead" SiliconValley.com(online)2002 (Retrived on Apr. 29, 2002) Retrived from the Internet:<URL:http://www.siliconvalley.com/mld/news>.
Stikeman, Alexander. "Make the Diagnosis." Technology Review (online) 2002. (Retrived on May 23, 2002) Retrived from the Internet:<URL:http://www.technologyreview.com>.
Ohr, Stephan."Sensors seen enabling new-age services." EETimes (online) 2002 (Retrived on May 23, 2002) Retrived from the Internet: <URL:www.eet.com/printablearticle?doc_id>.
Stikeman, Alexander. "The State of Biomedicine" Technology review (online)2002. (Retrived on Jun. 5, 2002) Retrived from the Internet:<www.technologyreview.com/articles/stateof>.
The Ethics of Patenting DNA. The Nuffield Council on Bioethics 2002. The Nuffield Foundation (London, England).
"Technology shapes tommorrow's digital hospital." EETimes (online)2002 (Retrived on Jul. 5, 2002) Retrived from the Internet:<URL:htttp://eet.com/printablearticle?doc_id--OEG2002>.
Landro, Laura. The Hospitals Technology gap widens. The Wall Street Journal. Jul. 16, 2002. p. D3.
Rostler, Suzanne."Study finds drug errors common in U.S. Hospitals."Returs.com (online) 2002 (Retrived on Sep. 9, 2002) Retrived from the Internet: <reuters.com/printerfriendly.html?type=healthnews>.
Johnson, Colin. :Synthesis of nanoparticles coming into foucs. EETimes (online) 2002. (Retrived on Jul. 17, 2002) Retrived from the internet:<URL:www.eet.com/story/OEG2002>.
Philipkoski,Kristen. "BiochipLDiagnosis in a Pinch."Wired News (online) 2002. (Retrived on Jul. 18, 2002) Retrived from the Internet:<www.wired.com/news/print/0,1294,53861,00>.
"Wyeth Updates Product Labels for its Postmenopausal Harmone Therapies."WyethCorp. (online) 2002 (Retrived on Sep. 6, 2002) Retrived from the Internet:<www.wyeth.com/news/press>.
Pearson, Helen. At Home DNA Tests Are Here. The Wall Street Journal. Jun. 25, 2002 p. D6.

Johnson, Colin. "Silicon Nanoparticles Eyed for Chemical Detection."EETimes(online) 2002. (Retrived on Sep. 9, 2002)Retrived from the Internet:<www.eet.com/printablearticle?doc_id>.
Veloso, Mario et al.From Hospital Information System components to the Medical Record & Clinical Guidelines Protocols.Medical Informatics Europe'97.1997 p. 300(IOS,Amsterdam).
"Emerging Infections and Potential Bioterrorist Agents." UAB (online) 2001 (Retrived on Jan. 7, 2002) Retrived from the Internet:<www.bioterrorism.uab.edu/emerging infection>.
Miller,Krista at al. "I3C Tech Architecture."I3C(online)2002. (Retrived on 2002) Retrived from the Internet: <URL:http://www.i3c.org>.
Draetta,Giulio and Boisclair, Michael. Molecular Bioscreening in Oncology 2002 p. 356-367.
"Cancer Bioinformatics Infrastructure Objects (caBio)" National Cancer Institute Center for Bioinformatics (online)2002. (Retrived on 2002) Retrived from the Internet: <URL:http://ncicb.nci.nih.gov/core/caBIO>.
"Will pharmacogenovics revolutionize clinical trials?" Datamonitor (online) 2002. Retrived from the Internet: <URL:http://www.datamonitor.com-3573982C452997011c2oa~/home>.
"Bioinformatics glossary."Genomic Glossaries (online) 2002 (Retrived on Aug. 27, 2002) Retrived from the Internet:<URL:www.genomicglossaries.com/content/printpage.asp?REF=/Bioinf>.
"The new word in designer drugs." bmj(online) 1998 (Retrived on Jun. 27, 2002) Retrived from the Internet: <URL:http://www.bmj.com/cgi/content/full/316/7149/1930>.
"Commercialization-Putting Our discoveries to work." DNA Sciences (online) 2002. (Retrived on Jul. 20, 2002) Retrived from the Internet:URL:http://www.ppgx.com/sciencediscovery.jsp?site=dna& link = commercialization>.
"Philips Launches software to Pinpoint cancer." Reuters(online) 2002 (Retrived on Oct. 10, 2002) Retrived from the Internet:<www.reuters.com/printerfriendly.jhtml?type=technolog>.
"Biosensor/Transducer technology."Standford Biodesign (online) 2002(Retrived on Sep. 12, 2002)Retrived from the Internet:<www.Stanford.edu/group/biodesign/technical/overview.html>.
"Exact sciences issued Patent for Novel Method of Detecting Mutation." Exact Sciences (online) 2002.(Retrived on Sep. 19, 2002) Retrived from the Internet: <www.exactsciences.com/about/press_releases/exact&sciences&issued&patent&for&novel&method>.
"Metabolomics in biotech: A revolutionary tool to optimize the production of new leads."TNO pharma (online)2002(Retrived on Apr. 11, 2002) Retrived from the Internet:<www.pharm.t>.
"I3C Technical Meeting Agenda." I3C Consortium (online) 2002 (Retrived on Oct. 14, 2002) Retrived from the Internet:<URL:http://www. I3c.org/mtg/past.asp>.
"I3C Backgrounder." I3C Consortium (online) 2002.(Retrived on Oct. 14, 2002) Retrived from the Internet:<URL: http://i3c.org/html/i3c_backgrounder.html>.
Neumana, Eric et al. "I3C Pathways." I3C Consortium (online) 2002. (Retrived on Oct. 14, 2002) Retrived from the Internet:<URL:http://www.i3c.org>.
O'Reily Bioinformatics Technology Conference I3C Consortium (online) 2002 (Retrived on Oct. 14, 2002) Retrived from the Internet: <URL:http://www.i3c.org>.
Abate, Tom. "Proofreading the Human Genome." The SanFrancisco Chronicle. Oct. 7, 2002 p. E1.
Willing, Richard. "DNA Testing Fails to Live up to Potential." USA Today Oct. 7, 2002 p. 1A.
"Comparisons of Mutagenesis Kits." Stratagene Corporation. Advertisement 2002.
Lesko, Li et al. "Pharmacogenomic-guided drug development:regulatory perspective." The Pharmacogenomics Journal 2002 (2) p. 20-24.
Sannes, Lucy. "High-Content Screening:Parallel analysis Fuels Accelerated Discovery and Development."Cambridge Health Reports 2002.Cambridge Health Institute.(Upper falls, MA).
Landro, Laura. "Doctors Need Computerisez Offices". The Wall Street Journal. Sep. 5, 2002, pp. D4. Dow Jones & Company, New York, NY.

(56) References Cited

OTHER PUBLICATIONS

DxS Limited, 48 Grafton Street, Manchester M13 9xx United Kingdom, "Clinical, Diagnostic and Research Services," <www.dxsgenotyping.com>.
DxS Limited, "SNPs-Primed and Ready to Glow:Pharmacogenomic services enabled by Scorpions™ 'mix and glow' technology," <www.dxsgenotyping.com> 48 Grafton St., Manchester, UK.
Krishnan, S. et al., "A Multimedia-Based Medical Database Network System for Special Clinical Procedures in Healthcare Delivery", IEEE/EMBS, Oct. 30-Nov. 2, 1997. Chicago IL.
Little, Stephen, "Strategic options for delivering pharmacogenomic tests to the patient". GOR, Feb. 25, 2002, vol. 4, No. 1, Manchester, UK.
KK Jain "Applications of Biochip and Microarray Systems in Pharmacogenomics." Pharmacogenomics (2000) vol. 1 No. 3, p. 289-307.
Vanderlubbe, R.P., "Flexible Electronic Patient record: first results from a dutch hospital", Medical Informatics Europe '97, 1997. p. 246-251 (IOS, Amesterdam).
Bernadette Tansey, "Power Tools for the gene age," San Francisco Chronical, Feb. 7, 2005, E.
Ron Winslow & Anna Wilde Mathews, "New Genetic Tests Boost Impact of Drugs," Wall Street Journal, Dec. 21, 2005; D1.
Sharapov, Ilya, "Computational Applications for Life Sciences on Sun Platforms:Performance Overview," Market Development Engineering, Sun Microsystem, Inc., Nov. 2001.
"SNPs & other genetic variations glossary." Genomic Glossaries[online] Aug. 27, 2002] www.genomicglossaries.com/content/printpage.
"Pharmacogenomics: Medicine & the New Genetics." Human Genome Project Information 2002. www.ornl.gov/hgmis/medicine/pharma.html> US Dept. of Energy, Oakridge, TN.
U.S. Appl. No. 10/277,213, filed Oct. 18, 2002, Fernandez.
Lennard et al., "Congenital Thioupurine Methyltransferase Deficiency and 6-Mecaptopurine Toxicity During Treatment for Acute Lymphoblastic Leukaemia," Arch. Dis. Child. (1993) vol. 69, pp. 577-579.
U.S. Appl. No. 10/646,682, filed Aug. 22, 2003, Fernandez.
U.S. Appl. No. 11/140,438, filed May 26, 2005, Fernandez.
U.S. Appl. No. 11/585,519, filed Oct. 23, 2005, Fernandez.
U.S. Appl. No. 11/703,508, filed Feb. 6, 2007, Fernandez.
U.S. Appl. No. 12/115,508, filed May 5, 2008, Fernandez.
U.S. Appl. No. 12/239,563, filed Sep. 26, 2008, Fernandez.
U.S. Appl. No. 12/351,358, filed Jan. 9, 2009, Fernandez.
U.S. Appl. No. 11/703,331, filed Feb. 6, 2007, Fernandez.
U.S. Appl. No. 11/285,920, filed Nov. 23, 2005, Fernandez.
U.S. Appl. No. 11/385,058, filed Mar. 20, 2006, Fernandez.
U.S. Appl. No. 11/644,420, filed Dec. 22, 2006, Fernandez.
U.S. Appl. No. 11/949,256, filed Dec. 3, 2007, Fernandez.
U.S. Appl. No. 12/239,026, filed Sep. 26, 2008, Fernandez.
U.S. Appl. No. 12/114,664, filed May 2, 2008, Fernandez.
U.S. Appl. No. 12/423,230, filed Apr. 14, 2009, Fernandez.
U.S. Appl. No. 12/423,275, filed Apr. 14, 2009, Fernandez.
U.S. Appl. No. 12/423,340, filed Apr. 14, 2009, Fernandez.
U.S. Appl. No. 12/423,420, filed Apr. 14, 2009, Fernandez.
U.S. Appl. No. 12/423,548, filed Apr. 14, 2009, Fernandez.
U.S. Appl. No. 12/423,591, filed Apr. 14, 2009, Fernandez.
Davis, Alison, et al., "Pharmacogenetics Research Network and Knowledge Base: 1st Annual Scientific Meeting," Apr. 25, 2001, Bethesda, Maryland.
Healey, Jennifer and Gould, Grant, "Affective Jewelry and other Affective Accessories". M.I.T Media Laboratory, Affective Computing Research Project [online], [retrieved on Jan. 18, 2003]. Retrieved from the internet: <URL: http://www.media.mit.edu/affect/AC_research/projects/affective_jewelry.html>, pp. 1-5.
Borkholer, David A.; Debusschere, Derek B.; Stenger, David; and Kovacs, Gregory T.A., "Hybrid Biosensors". Stanford University Transducers Lab. Hybrid biosensers Project [online], [retrieved on Jan. 18, 2003]. Retrieved from the internet: <URL: http://transducers.stanford.edu/Projects.html>, pp. 1-4.
Tonnesen, Cindy and Withrow, Gary, "Biosensors". The Encyclopedia of virtual Environments [online] [retrieved on Jul. 26, 2006]. Retrieved from the internet: <URL: http://www.hitl.washington.edu/solvw/EVE/I.D.1.c.Biosensors.html>, pp. 1-8.

Debusschere, Derek B., and Kovacs, Gregory T.A., "Portable Cell-Based Biosensors". Stanford University Transducers Lab, Portable Cell-Based Biosensors Project [online], [retrieved on Aug. 8, 2003]. Retrieved from the internet: <URL: http:// transducers.stanford.edu/Projects.html>, pp. 1-3.
Ahn, Chong H. and Choi, Jin-Woo., "Plastic-Based Disposable Smart Biochips with Integrated Biosensors for Blood Analysis and Clinical Diagnostics".
University of Cincinnati Department of Electrical Engineering & Computer Engineering and Computer Science. MicroSystems and BioMEMS Lab.[retrieved on Aug. 8, 2003]. Retrieved from the internet: <URL: http://www.healthtech.com/2001/mfb/abstracts/ahn.html>, pp. 1-2.
Elias, Paul, "Biotech Inventors Turn to More Exotic Manipulation" Mail&Guardianonline [online], Jul. 8, 2003 [retrieved on Aug. 23, 2003]. Retrieved from the internet: <URL:http:// www.mg.com.za/articledirect.aspx?articleid=23935&area=%2fbreaking_news%2fbreaking_news_international_news%2f>, pp. 1-3.
Rogers, Jim and Quick, Julie, "USDA Strengthens 2003 Permit Conditions for Field Testing Genetically Engineered Plants". U.S.D.A. Press Release [online], [retrieved before or on Aug. 23, 2003]. Retrieved from the internet: <URL:http://aphis.usda.gov.Ipa.news/2003/03/gepermits_brs.html>, pp. 1-2.
Savello, Paul, "Food Safety in the Food Manufacturing Industry". USAID Kosovo Cluster & Business Support Project Press Release, Kosovo Business Support Archive Articles [online], article in "Koha Ditore," Dec. 11, 2002, Available on the Internet at: <http://usaidkcbs.com/KBS%20Archive/KBS%20Articles/121102.htm>, pp. 1-3. [Retrieved before or on Aug. 23, 2003].
"Laboratory Tests that Detect Cancer". The Cancer Cure Foundation [online], [retrieved before or on Aug. 23, 2003]. Retrieved from the Internet: <URL: http:// www.cancercure.org/tests_to_detect_cancer.htm>, pp. 1-10.
Tansey, Bernadette, "Cancer Sleuthing: Bay Area Companies among Those Profiling the Disease". SFGate.com [online], Jul. 6, 2003, [retrieved before or on Aug. 23, 2003]. Retrieved from the Internet: <URL:http:// www.sfgate.com/cgi-bin/article.cgi?f=/c/a/2003/07/06/BU246056.DTL&hw=Cancer+sleuthing&sn=001&sc=1000>, pp. 1-2.
"New Test May Improve Cancer Detection". Press Release from Reuters.com [online], [retrieved on Jul. 10, 2003], Retrieved from the internet: <URL: http://www.reuters.com/new/Article.jhtml?type=healthNews&StoryID=3112050&fromEmail=true>, 1 page; alternatively available from the internet: <URL: http:ww.cancerpage.com/news/article.asp?id=6132>, 1 page.
"Gene Profiling May Help Treat Cancer; Procedure Could Reduce Unnecessary Use of Certain Drugs", Press Release from MSNBC.com [online] [retrieved before or on Aug. 23, 2003]. Retrieved from the internet: <URL: http://www.msnbc.msn.com/id/3076856/>, pp. 1-4.
Medoro, Gianni; Manaresi, Nicolo; Tartagni, Marco; and Guerrieri, Roberto, "CMOS-only Sensors and Manipulators for Microorganisms", from IEEE Xplore.org [online], Aug. 6, 2002 [retrieved before or on Aug. 23, 2003]. Retrieved from the Internet: <URL: http://ieeexplore.ieee.org/xpls/absprintf.jsp?amumber=904344>, pp. 1-11.
"RNA Interference", Science & Technology Release by Sirna Therapeutics [online], [retrieved on Jul. 10, 2003] Retrieved from the Internet: <URL: http://www.sirna.com/wt/page/science>, pp. 1-2.
New Products—Targefect-siRNA Transfection Kit for RNA Intererence Studies Product Description from Targeting Systems, Santee (CA) [online], [retrieved on Jul. 10, 2003] Retrieved from the Internet: <URL: http://www.targetingsystems.com/siRNA.pdf>, pp. 1-8.
Atanasov, Plamen; Yange, S.; Salehi, C.; Ghindilis, Andrei; and Wilkins, EBTISAM, "Short-term Canine Implantation of Glucose Monitoring-Telemetry Device", Medical Engineering and Physics, vol. 18, No. 8 (1996), pp. 632-640.
"Medical Micromachines: New ATDC Company Developing Implantable Blood Pre and Flow Sensor Based on Micro Electromechanical Systems (MEMS) Technology", Press Release from Advanced Technology Development Center [online], Jan. 28, 2003 [retrieved before or on Aug. 23, 2003]. Retrieved from the internet: <URL: http://web.archive.org/web/20030210225423/www.atdc.org/news/january282002.html>, pp. 1-3.
Walli, Ron, "Miniature Implanatable Sensor Likely Lifesaver for Patients", News Release from Oak Ridge National Laboratory [online], retrieved before or on Aug. 23, 2003]. Retrieved from the

(56) References Cited

OTHER PUBLICATIONS internet: <URL: http://www.omi.gov/info/press_releases/get_press_release.cfm?ReleaseNumber=mr20021122-00> pp. 1-2.
"Research Presented at ADA Annual Meeting Demonstrates Accuracy and Feasibility of Artificial Pancreas Components", News Release from Meditronic [online] [retrieved before or on Aug. 23, 2003]. Retrieved from the internet: <URL: http://wwwp.meditronic.com/Newsroom/NewsReleaseDetails.do?itemid=1096480090589&lang=en_US>, pp. 1-3.
"IntelliSense Drives MEMS Product Design Development and Manufacturing", Sensor Business Project, vol. 9, No. 9 (Jan. 9, 2000), pp. 65-69, Vital Information Publications, Foster City, CA.
Dichter, Marc A., "An Implantable Device to Predict and Prevent Seizures", 2002 (abstract) National Institute of Neurological Disorders and Stroke [online], pp. 54-55. [retrieved on Aug. 8, 2003]. Retrieved from the internet: <URL: http://www.nibib.nih.gov/nibib/File/News%20and%20Events/Previous%20Symposia%20and%20Workshops/1516Aug2005/ABSTRACTS.pdf>.
Schwiebert, Loren, "Wireless Networking Solutions for Smart Sensor Biomedical Applications", 2000 (abstract). National Science Foundation [online], pp. 1-2, [retrieved on Aug. 8, 2003]. Retrieved from the internet: <URL: http://Shamir.eas.asu.edu/%7emcn/bioabstract.html>.
Eversmann, Bjorn; Jenkner, Martin; Paulus, Christian; Hofmann, Franz; Brederlow, Ralf; Holzapfl, Birgit; Fromherz, Peter; Brenner Marucus; Schreiter, Matthias; Gabl, Reinhard; Plehnert, Kurt' Steinhauser, Michael; Eckstein, Gerald; Schmitt-Landsiedel, Doris; Thewes, Roland, "A 128×128 CMOS Biosensor Array for Extracellular Recording of Neural Activity", IEEE Journal of Solid State Circuits, vol. 38, Issue 12 (2003), pp. 2306-2317.
"Chip Senses Trace DNA", Technology research News from an MIT Enterprise Technology Review [online], Jul. 31, 2003. [retrieved on Aug. 4, 2003]. Retrieved from the internet: <URL: http://www.technologyreview.com/>, 1 page.
Hui Du, Matthew D. Disney, Benjamin L. Miller, and Todd D. Krauss, "Hybridization-Based Unquenching of DNA Hairpins on AU Surfaces, Prototypical 'Molecular Beacon' Biosensors" JACS, J. Am. Chem. Soc., 125:4012-13 (2003).
"The Outcry over 'Terminator' Genes in Food," Business Week on line, pp. 1-3 retrieved Jul. 14, 2003, <www.businessweek.com/print/magazine/content/03_28/b3841091.htm>.
"More Delicious Delicacies, Thanks to Tech," Business Week on line, pp. 1-3, retrieved Jul. 18, 2003, <www.businessweek.com/print/technology/content/jul2008/tc2003078>.
"Food Scientists to Assess Bioterrorism Risk," Reuters, Jul. 15, 2003; at <www.reuters.com> retrieved Jul. 15, 2003, one page.
Hao Wu, William N. Hait, and Jin-Ming Yang, "Small Interfering RNA-Induced Suppression of MDR1 (P-Glycoprotein) Restores Sensitivity to Multidrug-resistant Cancer Cells"; Cancer Research, 63:1515-1516 (Apr. 1, 2003).
Raja Mishra, "Advances Begin to Tame Cancer," retrieved Jul. 6, 2003, <www.boston.com/dailyglobe/187/metro/advances>; 5 Pages.
Tony Strattner, "Genomic Advances of Past Decade are Real: Ordonez" Bio-IT World, <www.imakenews.com/health-itworld/e_article000165177.cfm?x=a1vsry1,avfsry1>Retrieved Jul. 10, 2003 (3 pages).
Ouellette, Jennifer, "Biosensors: Microelectronics Marries Biology" The Industrial Physicist, pp. 11-12; 14; Sep. 1998 (c) American Institute of Physics.
Maggie Fox, "Cell-based Detector Lights up for Deadly Gems," Reuters, <www.reuters.com>, retrieved Jul. 10, 2003, 2 pages.
Maggie Fox, "US Team Finds Hints of How, Why Cancer Spreads," Reuters, <www.reuters.com>, retrieved Jul. 12, 2003, pp. 1-10.
Zuckerman, Laurie, "Taking the Guesswork out of Cancer Treatment Sicel Technologies," Business Leader, Sicel Technologies, 12(4):20 (Oct. 10, 2000). Abstract.
Anand Ramakrishnan and Ajit Sadana, "A Mathematical Analysis Using Fractals for Binding Interactions of Nuclear Estrogen Receptors Occurring on Biosensor Surfaces," Analyt. Biochem., 303:78-92 (2002), Chemical Engineering Department, University of Mississippi.

David Perlman, "Gene Variant Tied to Increased Susceptibility to Cancer, Research Finds Other Factors are Also Part of Equation," Wed., Aug. 6, 2003,<sfgate.com/cgi-bin/article.cgi?f=/c/a/2003/08/06/mn131526.dtl (p. 1-2).
Rhonda Ascierto, "Canary Chip Warns of Danger From Bioagents," <www.svbizink>; Fri., Jun. 20, 2003. (p. 1-2).
"Microarrays & Protein Chips Glossary," <www.genomicglossaries.com/content/printpage.asp?REF=/content/microarrays&protein> retrieved Jun. 27, 2003; (p. 1-20).
Microarrays & Protein Chips Categories, <www.genomicglossaries.com/content/printpage.asp?REF=/content/microarrays&protein> retrieved Jun. 27, 2003; (p. 1-23).
"Sirna Therapeutics: RNAI," Sirna Therapeutics, <www.sirna.com/rnai/rnai/html>, retrieved Jul. 10, 2003.
Ma, Xiao-Jun., et al., "Gene expression profiles of human breast cancer progression." Proceedings of the National Academy of Sciences of the United States of America [online], Nov. 9, 2002 [retrieved on Jul. 1, 2009]. Retrieved from the Internet: <URL: http://www.pnas.org/content/100/10/5974.abstract>.
U.S. Appl. No. 12/541,146, filed Aug. 13, 2009, Fernandez, Dennis S.
"Clinical Services." DxS Limited. 2003 (online). Manchester, United Kingdom. Retrieved from the Internet: <URL: http://www.dxsgenotyping.com>.
Oetting, W. S. et al., "Linkage Analysis with Multiplexed Short Tandem Repeat Polymorphisms Using Infrared Fluorescence and M13 Tailed Primers", Genomics, 1995, vol. 30, pp. 450-458, Elsevier, Amsterdam/The Netherlands.
Weber, Wendell, "The Legacy of Pharmacogenetics and potential Applications", (2001), pp. 1-18, vol. 479, Elsevier.
Schoeneberg, T. et al., "Mutant G-protein-coupled receptors as a cause of human diseases", Pharmacology & Therapeutics, 2004, pp. 173-206, vol. 104, Elsevier, Amsterdam/The Netherlands.
"Delivering Pharmacogenomics. "DxS Limited. 2003 (online). Manchester, United Kingdom. Retrieved from the Internet: <URL: http://www.dxsgenotyping.com>.
GENSET, "Business Opportunities Pharmacogenomics: The Science of the Drug Response Genes," [retrieved on Jun. 27, 2002] Retrieved from the Internet: <URL: www.genxy.com>.
Chang, Chen. "BLAST Implementation on BEE2," Electrical Engineering and Computer Science, Univ. of Cal Berkeley, 2004.
Jacobi, Ricardo P., et al., "Reconfigurable Systems for Sequence Alignment and for General Dynamic Programming," Genet. Mol. Res. 4(3):543-552 (Sep. 30, 2005).
Wood, A., "Racial Differences in the Response to Drugs—Pointers to Genetic Differences", New England Journal of Medicine, May 3, 2001, pp. 1393-1396, vol. 344, No. 18, Massachusetts Medical Society, Waltham, Mass/US.
Han M., et al. "Quantum-dot-tagged microbeads for multiplexed optical coding of biomolecules", Nature Biotechnology, 2001, pp. 631-635, Jul. 2001, vol. 19, <URL: http://www.genxy.com/Business/bus_pharmaco.html>.
Sandra J. Rosenthal, "Bar-coding biomolecules with fluorescent nanocrystals", Nature Biotechnology, 2001, pp. 621-622.
Merriam Webster Online Dictionary "Join" [Retrieved from the Internet on Feb. 12, 2008: <URL:http://www.merriam-webster.com/dictionary/join>.
"Couple." Merriam-Webster Online Dictionary. Retrieved from the internet on Jul. 17, 2007 <URL: http://www.merriam-webster.com/dictionary/couple>.
Easterling, et al., "Comparative Analysis of Software for Physiologically Based Pharmacokinetic Modeling: Simulation, Optimization, and Sensitivity Analysis, Toxicology Methods", Jul. 2000, vol. 10, Issue 3, pp. 203-220.
GenCore version 6.3, USPTO Examiner's search, Run on Sep. 1, 2010 on "OM nucleic—nucleic search, using sw model".
Kricka, Larry J., "Miniaturization of Analytical Systems," Clinical Chemistry (1998) vol. 44, No. 9, pp. 2008-2014.

\* cited by examiner

PHARMACO-GENOMIC MUTATION LABELING

CROSS-REFERENCE TO RELATED APPLICATION

This application is a divisional of US patent application U.S. patent application Ser. No. 10/277,213 filed on Oct. 18, 2002.

FIELD OF INVENTION

Field covers electronic labeling apparati and methods, particularly for pharmaco-genomic mutation.

BACKGROUND

In various healthcare applications, labels are used to identify patients, medicines, and other medical items and information. Traditionally, however, medical labels are generally static, i.e., fixed in informational content, and often constructed of paper or similar material, which are then attached mechanically to adhere to certain object patient or medicine. Because traditional labeling systems are inefficient, and sometimes prone to staff error, there is need for improved approach. Moreover, in view of emerging technical and informational complexities arising from genomic-based practice, there is further need for improved labeling scheme.

SUMMARY

Electronic label processor, which compares bioinformatic values to determine pharmaco-genomic mutation, displays the mutation. Labels are network-accessible for modified medical messages. Bioinformatic values are determined preferably at different times.

BRIEF DESCRIPTION OF FIGURES

The accompanying drawings, which are incorporated in and form a part of this specification, illustrate embodiments of the invention and together with the description, serve to explain the principles of the invention.

DETAILED DESCRIPTION

Figure 1A:
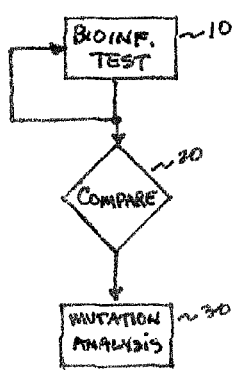
FIG. 1A flow chart shows representative steps for pharmaco-genomic mutation labeling method.

As understood and defined herein, term "pharmaco-genomic mutation" is understood generally and broadly to mean an alteration, variation, polymorphism, or other detectable or measurable change from a naturally-occurring, normal, engineered, induced or previously-mutated condition in single or multiple target or candidate nucleic acid, oligonucleotide or regulatory sequence, gene of interest or under investigation, protein sequence or folding structure, enzyme or other biomolecular material obtained from a host cell or tissue sample, or any segment or region of DNA which may be transcribed into RNA, contain an open reading frame, encode a protein, and include one or more DNA regulatory element to control expression of a transcribed region. Such mutation is not necessarily indicative of pharmaceutical function or effect, but may be indicative of genomic, kinetic, proteomic, or metabolomic instability or loss of heterozygosity, for example; and refer to any mutation associated with disease, such as cancer or other pathological mono- or polygenic condition, disorder or syndrome. Such mutation term may comprise any single or multiple nucleotide insertion, deletion, rearrangement, transition, translation, tranversion, substitution, frame-shifting, repeat, or chromosomal rearrangement.

Moreover, term "bioinformatic value" is understood generally and broadly to mean one or more digital or analog data-structure, text, object, signal, marker, code, tag, map, or other electronically-representable information, meta-information, or annotation that refers, corresponds, indicates, suggests, or is otherwise associated with a pharmaco-genomic mutation, or associated expression or pathway thereof, that is detected, measured, or otherwise determined to apply or be associated phenotypically with a given host, or host group, or biological material obtained or derived therefrom. Such value may be electronically stored, accessed, indexed, displayed, visualized, transmitted, modified, updated, compressed, secured, mined, searched, modeled, screened, profiled, or otherwise computationally processed.

For example, in accordance with mutation labeling or epidemiological aspect of present invention, one or more bioinformatic value may be determined from sensor or other host information to indicate presence or suggest risk of pharmaco-genomic mutation, such as disease or disorder related to hemoglobin, trinucleotide repeat expansion, micro-deletion syndrome, leukemia or solid tumor, metabolism (e.g., carbohydrate, amino acid, lipid, organic acid, urea cycle, energy production, or heavy metal transport disorder or defect), mucopolysaccharidoses, lysosomal storage, major histocompatibility complex, birth defect or syndrome, cancer, coronary heart disease.

Such pharmaco-genomic mutation may be determined or suggested by various sensor or related processing (e.g., Southern blotting, direct DNA sequencing, SSCP analysis, DGGE analysis, DNA mismatch cleavage, ASO hybridization, mass spectrometry, DNA chip hybridization, protein truncation, or other detection or sensing approach) described herein for determining bioinformatic value.

Generally, labeling system and process are embodied using one or more devices associated with one or more hosts. In accordance with one aspect of the present invention, such devices indicate when some genetic or other biological change is determined. For example, such change may be a genetic sequence mutation that is detected when comparing a prior sequence with another sequence. Each device may generate some indication, such as a visible or audible alert that reports such change.

Mutation labels alert medical professionals in prioritized or hierarchical manner, such that higher-risk likelihood or more serious toxicity or patient risk are revealed graphically or audibly through I/O 48 in emphasized or highlighted context. Such alert may further indicate or warn when wrong or inappropriate medication was or is delivered to particular patient having pharmaco-genomic profile.

Figure 1B:
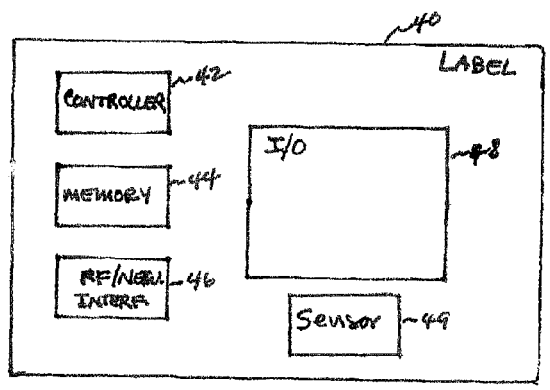
FIG. 1B shows generalized diagram of pharmaco-genomic mutation label apparatus.

FIG. 1A flow chart shows representative steps for pharmaco-genomic mutation labeling method. Electronic label processor or device electronically compares 20 bioinformatic values or data to one or more tested bioinformatic value or data 10 to determine pharmaco-genomic mutation and analysis 30, or clinical optimization associated with host. FIG. 1B shows generalized diagram of pharmaco-genomic mutation label apparatus 40. Label input/output display 48 indicates pharmaco-genomic mutation, which may be network-accessible through wired, wireless or radio-frequency (RF) network communication interface 46 for modified medical message. Bioinformatic values are stored remotely or locally in memory 44 and determined or otherwise processed by controller or microprocessor 42 preferably at different times using sensor 49.

Figure 1C:
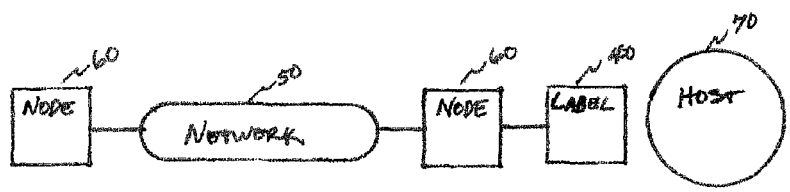
FIG. 1C shows sample pharmaco-genomic mutation labeling system and network.

Optionally, label apparatus 40 is embodied in one or more mainframe computer, engineering workstation, personal computer, network processor, patient-attached, local, adjacent or hand-held or mobile personal digital assistant device, embedded controller, or other digital signal processing machine capable of electronic storage, display, and access to network or sensor elements. FIG. 1C shows sample pharmaco-genomic mutation labeling system and network 50 with multiple nodes 60 coupled thereto, as well as label apparatus 40, which is associated with biological or tissue host 70.

Optionally, label apparatus 40 couples to or includes one or more sensor 49 for detecting, testing, screening, or generating a pharmaco-genomic mutation, bioinformatic value, or lack thereof, associated with a particular host, or biomaterial therefrom in vitro or in vivo. Preferably, in vivo implantable sensor or label packaging is constructed to be nonthrombogenic and nontoxic.

For example, sensor 49 may comprise one or more integrated nucleic acid diagnostic device, assay, or array of nucleic acid probes on biological chips or plates, available commercially from Affymetrix, Inc. (Santa Clara, Calif.), capable of sample acquisition and analysis for nucleic acid-based diagnostic, de novo sequencing, or detecting reaction between target molecules and probes.

Sensor 49 may also comprise one or more miniature, implantable identification device or "VeriChip", available commercially from Applied Digital Solutions, Inc. (Palm Beach, Fla.), capable of generating host or patient or medical information and other bioinformatic values.

It is further contemplated herein that sensor 49 may also employ one or more system or method for detecting or generating pharmaco-genomic mutation or bioinformatic value using integrated chip refractive-index micro-interferometry detection, using coherent VCSEL, laser diode, or He–Ne laser source, etched substrate capillary channel for sample reception and analysis, and reflected laser-light reflection photodetector; or affinity-based biosensor based on optical evanescent wave detector using flow-based surface plasmon resonance in micro-fabricated integrated fluidic cartridge to capture tagged proteins, thiol coupling, or coil-coil interaction, wherein resonance angle is continuously monitored to detect changes in refractive resonance angle and refractive index corresponding to changes in mass when certain ligand binds to, or dissociates from, immobilized binding partner.

Also sensor 49 may detect or generate pharmacogenomic mutation or bioinformatic value using semiconductor nanocrystal or so-called quantum-dot device as detectable label or probe by linking or bonding to one or more affinity molecules of a detectable substance in an analyte, whereupon such nanocrystal probe in response to a first energy associated with a presence of detectable substance within material bonded to the probe, excites the nanocrystal in the probe and causes the probe to provide a second energy or generate or fluoresce a distinct wavelength signal indicating the presence.

It is further contemplated herein that sensor 49 may employ one or more system or method for detecting or generating pharmaco-genomic mutation or bioinformatic value using mass spectrometry, or native enzyme or antibody reactions for protein sequencing or detection; or chromatographic on-chip separation with mass spectrometry using surface enhanced laser desorption and ionization time of flight mass spectrometry, available commercially from Ciphergen Biosystems (Palo Alto, Calif.), using chip array to detect protein biomarkers indicative of disease.

Also sensor 49 may detect or generate pharmacogenomic mutation or bioinformatic value using one or more micro-electrical-mechanical or molecular systems, devices, probes, or arrays, or assays structurally comprising dendrimer, buckyball, fullerene, wire, or nanotube, for example, to monitor, detect, control, or otherwise process electrically, mechanically, optically, or chemically biological or genetic molecules, or contaminant agents or indicators thereof, such as anthrax, smallpox, botulism, tularemia, viral hemorrhagic fever, or plague.

Optionally, pharmaco-genomic mutation or bioinformatic value is indicated, determined, or generated, in part, by detecting alteration in target nucleic acid, described by Shuber in U.S. Pat. No. 6,428,964; by identifying mutation in gene of interest without phenotypic guide, described by Goodfellow in U.S. Pat. No. 5,994,075; by identifying genes underlying defined phenotypes, described by Iris et al in U.S. Pat. No. 6,221,585; by using computer program and database structure for detecting molecular binding events, described by Hefti in U.S. Pat. No. 6,395,480; by using computer-assisted method and apparatus for identification and characterization of biomolecules in biological sample, described by Parekh et al. in U.S. Pat. No. 6,064,754; or using methods, software, and apparatus for identifying genomic regions harboring gene associated with detectable trait, described by Schork et al. in U.S. Pat. No. 6,291,182; which references are hereby incorporated by reference as appropriate.

Furthermore, it is contemplated herein that pharmaco-genomic mutation or bioinformatic value may be indicated, determined, or generated using various mutation detection techniques, and applicable sensor and processes therefore, such as:

Southern blotting (to detect insertions, deletions, and rearrangements, as well as ordering of DNA fragments into physical map), using DNA digestion with restriction enzyme, resolution of fragments with agarose gel electrophoresis, transfer of DNA to nylon membrane and hybridization of labeled probe to DNA fragments;

Direct DNA sequencing (to detect insertions, deletions, point mutations, and rearrangements), using determination of linear order of nucleotides of test DNA, specific nucleotide detected by chemical cleavage, dideoxychain termination, or fluorochorome dye;

Single-strand conformational polymorphism (SSCP) analysis (to detect small insertions or deletions, and point mutations), using differential electrophoretic mobility of single-stranded test DNA with different secondary structures or conformations through non-denaturing gel;

Denaturing gradient gel electrophoresis (DGGE) analysis (to detect small insertions or deletions, and point mutations), using migration of DNA duplexes through electrophoretic gel with increasing amounts of denaturant (e.g., chemical, temperature) until DNA strands separate; resolution of alleles by Polyacrylamide gel electrophoresis (PAGE);

DNA mismatch cleavage (to detect small insertions or deletions, and point mutations), using hybridization of labeled proe to test DNA, cleavage of DNA at site of base-pairing mismatch;

Allele-specific oligonucleotide (ASO) hybridization (to detect allele(s) of known composition), using preferential hybridization of labeled probe to test DNA with uniquely complementary base composition;

Mass spectrometry (to detect small insertions or deletions, and point mutations), using detection of physical mass of sense and anti-sense strands of test DNA;

DNA chip hybridization (to detect test DNA of known composition), using hybridization of test DNA to arrays of oligonucloeotides ordered on silicon chip; or Protein truncation (to detect frameshift, splice site, or nonsense mutations that truncate protein product), using test RNA to make cDNA by reverse transcriptase-Polymerase Chain Reaction (TR-PCR) with 5' primer containing T7 promoter, cDNA translated and product resolved by sodium dodecyl sulfate (SDS)-PAGE.

Optionally, pharmaco-genomic mutation or bioinformatic value is indicated, determined, or generated, in part, to describe or suggest one or more hemoglobin disease, disorder, or risk, such as:

sickle cell disease, associated with or corresponding to β-globin missense mutation;

Hb H disease, associated with or corresponding to deletion or abnormality of three of four α-globin genes;

Hydrops fetalis (Hb Barts), associated with or corresponding to deletion or abnormality of all four α-globin genes;

β°-Thalassemia, associated with or corresponding to nonsense, frameshift, or slice site donor or acceptor mutations, and no β-globin production; or β⁺-Thalassemia, associated with or corresponding to missense, regulatory, or splice site consensus sequence or cryptic splice site mutation(s), and small of amount of β-globin production.

Optionally, pharmaco-genomic mutation or bioinformatic value is indicated, determined, or generated, in part, to describe or suggest one or more disease, disorder, or risk associated with trinucleotide repeat expansions, such as:

Category 1:

Huntington disease, associated with or corresponding to exon-located CAG repeat sequence of 36 to 100 or more (normal: 6 to 34);

Spinal and bulbar muscular atrophy, associated with or corresponding to exon-located CAG repeat sequence of 40 to 62 (normal: 11 to 34);

Spinocerebellar ataxia, type 1, associated with or corresponding to exon-located CAG repeat sequence of 41 to 81 (normal: 6 to 39);

Spinocerebellar ataxia, type 2, associated with or corresponding to exon-located CAG repeat sequence of 35 to 59 (normal: 15 to 29);

Spinocerebellar ataxia, type 3 (Machado-Joseph disease), associated with or corresponding to exon-located CAG repeat sequence of 68 to 79 (normal: 13 to 36);

Spinocerebellar ataxia, type 6, associated with or corresponding to exon-located CAG repeat sequence of 21 to 27 (normal: 4 to 16);

Spinocerebellar ataxia, type 7, associated with or corresponding to exon-located CAG repeat sequence of 38 to 200 (normal: 7 to 35);

Dentatorubral-pallidolusian atrophy/Haw River syndrome, associated with or corresponding to exon-located CAG repeat sequence of 49 to 88 (normal: 7 to 25);

Pseudoachondroplasia/multiple epiphyseal dysplasia, associated with or corresponding to exon-located GAC repeat sequence of 6 to 7 (normal: 5);

Oculopharyngeal muscular dystrophy, associated with or corresponding to exon-located GCG repeat sequence of 7 to 13 (normal: 6);

Cleidocranial dysplasia, associated with or corresponding to exon-located GCG GCT GCA repeat sequence of 27 (normal: 17);

Synpolydactyly, associated with or corresponding to exon-located GCG GCT GCA repeat sequence of 22 to 25 (normal 15);

Category 2:

Myotonic dystrophy, associated with or corresponding to CTG repeat sequence of 100 to several thousand (normal 5 to 37) in 3' untranslated region;

Friedreich's ataxia, associated with or corresponding to intron-located GAA repeat sequence of 200 to 900 or more (normal: 7 to 22);

Fragile X syndrome (FRAXA), associated with or corresponding to CGG repeat sequence of 200 to 2,000 or more (normal: 6 to 52) in 5' untranslated region;

Fragile site FRAXE, associated with or corresponding to GCC repeat sequence of 200 or more (normal: 6 to 35) in 5' untranslated region;

Spinocerebellar ataxia, type 8, associated with or corresponding to CTG repeat sequence of 107 to 127 (normal: 16 to 37) in 3' untranslated region;

Spinocerebellar ataxia, type 12, associated with or corresponding to CAG repeat sequence of 66 to 78 (normal: 7 to 28) in 5' untranslated region; or Progressive myoclonic epilepsy, type 1, associated with or corresponding to 12-bp repeat motif of 30 to 75 (normal: 2 to 3) in 5' untranslated region.

Optionally, pharmaco-genomic mutation or bioinformatic value is indicated, determined, or generated, in part, to describe or suggest one or more disease, disorder, or risk associated with micro-deletion syndromes, such as:

Prader-Willi syndrome, associated with or corresponding to chromosomal deletion 15q11-13;

Langer-Giedeion syndrome, associated with or corresponding to chromosomal deletion 8q24;

Miller-Dieker syndrome, associated with or corresponding to chromosomal deletion 17p13.3;

DiGeorge anomaly/velo-cardio-facial syndrome, associated with or corresponding to chromosomal deletion 22q11;

Williams syndrome, associated with or corresponding to chromosomal deletion 7q1; or Aniridia/Wilms tumor syndrome, associated with or corresponding to chromosomal deletion 11p13.

Optionally, pharmaco-genomic mutation or bioinformatic value is indicated, determined, or generated, in part, to describe or suggest one or more disease, disorder, or risk associated with leukemias and solid tumors, such as:

Leukemias:

Chronic myelogenous leukemia, associated with or corresponding to chromosomal aberration t(9;22)(q34;q11);

Acute myeloblastic leukemia, associated with or corresponding to chromosomal aberration t(8;21)(q22;q22);

Acute promeolocytic leukemia, associated with or corresponding to chromosomal aberration t(15;17)(q22;q11-22);

Acute non-lymphocytic leukemia, associated with or corresponding to chromosomal aberration+8,-7,-5,del(5q), del(20q);

Solid Tumors:

Burkitt lymphoma, associated with or corresponding to chromosomal aberration t(8;14)(q24;q32);

Ewing sarcoma, associated with or corresponding to chromosomal aberration t(11;22)(q24;q12);

Meningioma, associated with or corresponding to chromosomal aberration Monosomy 22;

Retinoblastoma, associated with or corresponding to chromosomal aberration del(13)(q14); or Wilms tumor, associated with or corresponding to chromosomal aberration del(11)(p13).

Optionally, pharmaco-genomic mutation or bioinformatic value is indicated, determined, or generated, in part, to describe or suggest one or more disease, disorder, or risk associated with metabolism, such as:

Carbohydrate Disorders:
- Classical glactosemia, associated with or corresponding to mutant gene product galactose-1-phosphate uridyl transferace at chromosomal location 9p13;
- Hereditary fructose intolerance, associated with or corresponding to mutant gene product fructose 1,6-biphospate aldolase at chromosomal location 9q13-q32;
- Fructosuria, associated with or corresponding to mutant gene product fructokinase at chromosomal location 2p23;
- Hypolactasia (adult), associated with or corresponding to mutant gene product lactase at chromosomal location 2q21;
- Diabetes mellitus (type I), associated with or corresponding to mutant polygenic products;
- Diabetes mellitus (type II), associated with or corresponding to mutant polygenic products;
- Maturity onset diabetes of youth (MODY), associated with or corresponding to mutant gene product glucokinase (60%) at chromosomal location 7p13;

Amino Acid Disorders:
- Phenylketonuria, associated with or corresponding to mutant gene product phenylalanine hydroxylase at chromosomal location 12q24;
- Tyrosinemia, type 1, associated with or corresponding to mutant gene product fumarylacetoacetate hydrolase at chromosomal location 15q23-25;
- Maple syrup urine disease, associated with or corresponding to mutant gene product branched-chain α-ketoacid decarboxylase (subunits at mutiple loci);
- Alkaptonuria, associated with or corresponding to mutant gene product homogentisic acid oxidase at chromosomal location 3q2;
- Homocystinuria, associated with or corresponding to mutant gene product cystathionine β-synthase at chromosomal location 21q2;
- Oculocutaneous albinism, associated with or corresponding to mutant gene product tyrosinase at chromosomal location 11q;
- Cystinosis, associated with or corresponding to mutant gene product CTNS at chromosomal location 17p13;
- Cystinuria, associated with or corresponding to mutant gene product SLC3A1 (type I) at chromosomal location 2p, or mutant gene product SLC7A9 (types II & III) at chromosomal location 19q13;

Lipid Disorders:
- MCAD, associated with or corresponding to mutant gene product medium-chain acyl-Coa dehydrogenase at chromosomal location 1p31;
- LCAD, associated with or corresponding to mutant gene product long-chain acyl-CoA dehydrogenase at chromosomal location 2q34-q35;
- SCAD, associated with or corresponding to mutant gene product short-chain acyl-Coa dehydrogenase at chromosomal location 12q22qter;

Organic Acid Disorders:
- Methylmalonic acidemia, associated with or corresponding to mutant gene product methylmalonyl-CoA at chromosomal location 6p;
- Propionic acidemia, associated with or corresponding to mutant gene product propionyl-CoA carboxylase at chromosomal location 13q32, 3q;

Urea Cycle Defects:
- Ornithine transcarbamylase deficiency, associated with or corresponding to mutant gene product ornithine carbamyl transferase at chromosomal location Xp21;
- Carbamyl phosphate synthetase deficiency, associated with or corresponding to mutant gene product caramyl phosphate synthetase I at chromosomal location 2p;
- Argininosuccinic acid synthetase deficiency, associated with or corresponding to mutant gene product argininosuccinic acid synthetase at chromosomal location 9q34;

Energy Production Defects:
- Cytochrome C oxidase deficiency, associated with or corresponding to mutant gene product cytochrome oxidase peptides at multiple loci;
- Pyruvate carboxylase deficiency, associated with or corresponding to mutant gene product pyruvate carboxylase at chromosomal location 11q;
- Pyruvate dehydrogenase complex ($E_1$) deficiency, associated with or corresponding to mutant gene product pyruvate decarboxylase, $E_1\alpha$ at chromosomal location Xp22;
- NADH-CoQ reductase deficiency, associated with or corresponding to multiple nuclear genes at multiple loci;

Heavy Metal Transport Defects:
- Wilson disease, associated with or corresponding to mutant gene product ATP7B at chromosomal location 13q14;
- Menkes disease, associated with or corresponding to mutant gene product ATP7A at chromosomal location Xq13; or
- Hemochromatosis, associated with or corresponding to mutant gene product HFE at chromosomal location 6p21.

Optionally, pharmaco-genomic mutation or bioinformatic value is indicated, determined, or generated, in part, to describe or suggest one or more disease, disorder, or risk associated with mucopolysaccharidoses, such as:
- Hurler/Scheie, associated with or corresponding to mutant enzyme α-L-Iduronidase;
- Hunter, associated with or corresponding to mutant enzyme Iduronate sulfatase;
- Sanfilippo A, associated with or corresponding to mutant enzyme Heparan-N-sulfamidase;
- Sanfilippo B, associated with or corresponding to mutant enzyme α-N-Acetylglucosaminidase;
- Sanfilippo C, associated with or corresponding to mutant enzyme Acetyl-CoA: α-glucosaminide N-acetyltransferase;
- Sanfilippo D, associated with or corresponding to mutant enzyme N-Acetylglucosamine-6-sulfatase;
- Morquio A, associated with or corresponding to mutant enzyme N-Acetylglucosamine-6-sulfatase;
- Morquio B, associated with or corresponding to mutant enzyme β-Galactosidase;
- Maroteaux-Lamy, associated with or corresponding to mutant enzyme Aryl sulfatase B; or
- Sly, associated with or corresponding to mutant enzyme β-Glucuronidase.

Optionally, pharmaco-genomic mutation or bioinformatic value is indicated, determined, or generated, in part, to describe or suggest one or more disease, disorder, or risk associated with lysosomal storage, such as:
- Tay-Sachs, associated with or corresponding to mutant enzyme β-Hexosaminidase (A isoenzyme);

Gaucher (type I; non-neuropathic), associated with or corresponding to mutant enzyme β-Glucosidase;

Niemann-Pick, type 1A, associated with or corresponding to mutant enzyme Sphingomyelinase;

Fabry, associated with or corresponding to mutant enzyme α-Galactosidase;

GM1 gangliosidosis (infantile), associated with or corresponding to mutant enzyme β-Galactosidase;

Krabbe, associated with or corresponding to mutant enzyme β-Galactosidase (galactosylceramide-specific);

Metachromatic leukodystrophy (late-infantile), associated with or corresponding to mutant enzyme Aryl sulfatase A;

Sandhoff, associated with or corresponding to mutant enzyme β-Hexosaminidase (total);

Schindler, associated with or corresponding to mutant enzyme α-N-Acetylgalactosaminidase; or Multiple sulfatase deficiency, associated with or corresponding to mutant enzyme Aryl sulfatases A B C.

Optionally, pharmaco-genomic mutation or bioinformatic value is indicated, determined, or generated, in part, to describe or suggest one or more genetic disease, disorder, or risk such as:

α-1-Antitrypsin deficiency, associated with or corresponding to disease gene product serine protease inhibitor at chromosome location 14q;

α-Thalassemia, associated with or corresponding to disease gene product α-Globin component of hemoglobin at chromosome location 16p;

β-Thalassemia, associated with or corresponding to disease gene product β-Globin component of hemoglobin at chromosome location 11p;

Achondroplasia, associated with or corresponding to disease gene product fibroblast growth factor receptor 3 at chromosome location 4p;

Adult polycystic kidney disease, associated with or corresponding to disease gene products polycystin-1 membrane protein at chromosome location 16p, polycystin-2 membrane protein at chromosome location 4p;

Albinism, oculocutaneous (type 1), associated with or corresponding to disease gene product tyrosinase at chromosome location 11q;

Albinism, oculocutaneous (type 2), associated with or corresponding to disease gene product tyrosine transporter at chromosome location 15q;

Alzheimer disease, associated with or corresponding to disease gene products presenilin 1 at chromosome location 14q, presenilin 2 at chromosome location 1q, apo-lipoprotein E at chromosome location 19q, β-Amyloid precursor protein at chromosome location 21q;

Amyotrophic lateral sclerosis, associated with or corresponding to disease gene product superoxide dismutase 1 at chromosome location 21q;

Angelman syndrome, associated with or corresponding to disease gene product ubiquitin-protein ligase E3A at chromosome location 15q;

Ataxia telangiectasia, associated with or corresponding to disease gene product cell cycle control protein at chromosome location 11q;

Beckwith-Wiedemann syndrome, associated with or corresponding to disease gene product insulin-like growth factor II at chromosome location 11p;

Bloom syndrome, associated with or corresponding to disease gene product RecQ helicase at chromosome location 15q;

Breast cancer (familial), associated with or corresponding to disease gene products BRCA1 tumor suppressor at chromosome location 17q, BRCA2 tumor suppressor at chromosome location 13q;

Charcot-Marie-Tooth disease (type 1B), associated with or corresponding to disease gene product myelin protein zero at chromosome location 1q; (type 1A), associated with or corresponding to disease gene product peripheral myelin protein 22 at chromosome location 17p; (CMTX1), associated with or corresponding to disease gene product connexin-32 gap junction protein at chromosome location Xq;

Cystic fibrosis, associated with or corresponding to disease gene product cystic fibrosis transmembrane regulator (CFTR) at chromosome location 7q;

Deafness (nonsyndromic), associated with or corresponding to disease gene products connexin-26 gap junction protein at chromosome location 13q, actin polymerization regulator at chromosome location 5q, KCNQ4 potassium channel at chromosome location 1p.

Diabetes (MODY1), associated with or corresponding to disease gene product hepatocyte nuclear factor-4α at chromosome location 20q; (MODY2), associated with or corresponding to disease gene product glucokinase at chromosome location 7p; (MODY3), associated with or corresponding to disease gene product hepatocyte nuclear factor-1α at chromosome location 1q;

Duchenne/Becker muscular dystrophy, associated with or corresponding to disease gene product dystrophin at chromosome location Xp;

Ehlers-Danlos syndrome, associated with or corresponding to disease gene product collagen (COL3A1) at chromosome location 2q;

Ellis van Creveld syndrome, associated with or corresponding to disease gene product leucine zipper at chromosome location 4p;

Familial polyposis coli, associated with or corresponding to disease gene product APC tumor suppressor at chromosome location 5q;

Fragile X syndrome, associated with or corresponding to disease gene product FMR1 RNA-binding protein at chromosome location Xq;

Friedreich ataxia, associated with or corresponding to disease gene product Frataxin mitochondrial protein at chromosome location 9q;

Galactosemia, associated with or corresponding to disease gene product Galactose-1-phosphate-uridyltransferase at chromosome location 9p;

Hemochromatosis, associated with or corresponding to disease gene product transferring receptor binding protein at chromosome location 6p;

Hemophilia A, associated with or corresponding to disease gene product clotting factor VIII at chromosome location Xq;

Hemophelia B, associated with or corresponding to disease gene product clotting factor IX at chromosome location Xq;

Hereditary nonpolyposis colorectal cancer, associated with or corresponding to disease gene products MLH1 DNA mismatch repair protein at chromosome location 3p, MLH2 DNA mismatch repair protein at chromosome location 2p, PMS1 DNA mismatch repair protein at chromosome location 2q, PMS2 DNA mismatch repair protein at location 7p, MSH6 DNA mismatch repair protein at chromosome location 2p;

Hirschsprung disease (type 1), associated with or corresponding to disease gene product RET tyrosine kinase proto-oncogene at chromosome location 10q; (type 2), associated with or corresponding to disease gene product endothelin receptor type B at chromosome location 13q;

Huntington disease, associated with or corresponding to disease gene product huntingtin at chromosome location 4p;

Hypercholesterolemia (familial), associated with or corresponding to disease gene product LDL receptor at chromosome location 19p;

Long QT syndrome (LQT3), associated with or corresponding to disease gene SCN5A cardiac sodium channel at chromosome location 3p; (LQT2), associated with or corresponding to disease gene product HERG cardiac potassium channel at chromosome location 7q; (LQT1), associated with or corresponding to disease gene product KVLQT1 cardiac potassium channel α submit at chromosome location 11p; (LQT5), associated with or corresponding to disease gene product KCNE1 cardiac potassium channel β subunit at chromosome location 21q; (LQT6), associated with or corresponding to disease gene product KCNE2 cardiac potassium channel at chromosome location 21q;

Marfan syndrome, associated with or corresponding to disease gene product fibrillin-1 at chromosome location 15q;

Melanoma (familial), associated with or corresponding to disease gene products cyclin-dependent kinase inhibitor tumor suppressor at chromosome location 9p, cyclin-dependent kinase-4 at chromosome location 12q;

Myotonic dystrophy, associated with or corresponding to disease gene product protein kinase at chromosome location 19q;

Myoclonus epilepsy (Unverricht-Lundborg), associated with or corresponding to disease gene product cystatin B cystein protease inhibitor at chromosome location 21q;

Neurofibromatosis (type 1), associated with or corresponding to disease gene product neurofibromin tumor suppressor at chromosome location 17q; (type 2), associated with or corresponding to disease gene product merlin (schwannomin) tumor suppressor at chromosome location 22q;

Parkinson disease (familial), associated with or corresponding to disease gene product α-synuclein at chromosome location 4q;

Phenylketonuria, associated with or corresponding to disease gene product phenylalanine hydroxylase at chromosome location 12q;

Retinitis Pigmentosa, associated with or corresponding to disease gene products rhodopsin at chromosome location 3q, TULP1 tubby-like protein at chromosome location 6p, Retina-specific ABC transporter at chromosome location 1p, pheripherin at chromosome location 6p, rod outer segment membrane protein at chromosome location 11q, retinal rod photoreceptor cGMP phosphodiesterase β subunit at chromosome location 4p, retinal rod photoreceptor cGMP phosphodiesterase α subunit at chromosome location 5q, retinal rod cGMPgated channel α subunit at chromosome location 4p, myosin VIIA at chromosome location 11q;

Retinoblastoma, associated with or corresponding to disease gene product pRb tumor suppressor at chromosome location 13q;

Rett syndrome, associated with or corresponding to disease gene product methyl CpG binding protein at chromosome location Xq;

Sickle-cell disease, associated with or corresponding to disease gene product β-globin component of hemoglobin at chromosome location 11p;

Smith-Lemli-Opitz syndrome, associated with or corresponding to disease gene product 7-dehydrocholesterol reductase at chromosome location 11q;

Stargardt disease, associated with or corresponding to disease gene product ATP-binding cassette transporter at chromosome location 1p;

Tay-Sachs disease, associated with or corresponding to disease gene product hexosaminidase A at chromosome location 15q;

Tuberous sclerosis (type 1), associated with or corresponding to disease gene product hamartin tumor suppressor at chromosome location 9q; (type 2), associated with or corresponding to disease gene product tuberin tumor suppressor at chromosome location 16p;

Usher syndrome, associated with or corresponding to disease gene product myosin VIIA at chromosome location 11q;

Waardenburg syndrome (types 1 and 3), associated with or corresponding to disease gene product PAX3 transcription factor at chromosome location 2q; (type 2), associated with or corresponding to disease gene product MITF leucine zipper protein at chromosome location 3p; (type 4), associated with or corresponding to disease gene product endothelin 3 or endothelin B receptor at chromosome location 14q;

Wilms tumor, associated with or corresponding to disease gene product WT1 zind finger protein tumor suppressor at chromosome location 11p;

Wilson disease, associated with or corresponding to disease gene product copper transporting ATPase at chromosome location 13q; or von Willebrand disease, associated with or corresponding to disease gene product von Willebrand clotting factor at chromosome location 12q.

Optionally, pharmaco-genomic mutation or bioinformatic value is indicated, determined, or generated, in part, to describe or suggest one or more major histocompatibility complex (MHC) disease, disorder, or risk associated with MHC human leukocyte antigen (HLA)-associated allele, such as:

Type 1 diabetes, associated with or corresponding to allele DR3 and DR4;

Ankylosing spondylitis, associated with or corresponding to allele B27;

Narcolepsy, associated with or corresponding to allele DR2;

Celiac disease, associated with or corresponding to allele DR3, DR7;

Rheumatoid arthritis, associated with or corresponding to allele DR1, DR4;

Myasthenia gravis, associated with or corresponding to allele DR3, DR7;

Multiple sclerosis, associated with or corresponding to allele DR2;

Pemphigus vulgaris, associated with or corresponding to allele DR4;

Systemic lupus erythematosus, associated with or corresponding to allele DR2, DR3;

Hemochromatosis, associated with or corresponding to allele A3;

Malaria, associated with or corresponding to allele B53;

Graves disease, associated with or corresponding to allele DR3;

Psoriasis vulgaris, associated with or corresponding to allele Cw6; or

Squamous cell cervical carcinoma, associated with or corresponding to allele DQw3.

Optionally, pharmaco-genomic mutation or bioinformatic value is indicated, determined, or generated, in part, to describe or suggest one or more birth defect, syndrome, or risk associated with particular gene, such as:

Branchio-oto-renal syndrome, associated with or corresponding to gene BOR1;

Stickler syndrome, associated with or corresponding to gene COL2A1;

Schizencephaly syndrome, associated with or corresponding to gene EMX2;

Ellis-van Creveld syndrome, associated with or corresponding to gene EvC;

Creig syndrome, associated with or corresponding to gene GLI3;

Pallister-Hall syndrome, associated with or corresponding to gene GLI3;

Polydactyly type A syndrome, associated with or corresponding to gene GLI3;

Hand-foot-genital syndrome, associated with or corresponding to gene HOXA13;

Synpolydactyly syndrome, associated with or corresponding to gene HOXD13;

Piebaldism syndrome, associated with or corresponding to gene KIT;

Nail-patella syndrome, associated with or corresponding to gene LMX1;

Cleft lip/palate syndrome, associated with or corresponding to gene MSX1;

Multiple synostosis syndrome, associated with or corresponding to gene Noggin;

Ectrodactyly/ectodermal dysplasia syndrome, associated with or corresponding to gene p63;

Kidney and optic nerve defect syndrome, associated with or corresponding to gene PAX2;

Waardenburg syndrome, associated with or corresponding to gene PAX3;

Aniridia syndrome, associated with or corresponding to gene PAX6;

Oligodontia syndrome, associated with or corresponding to gene PAX9;

Rieger syndrome, associated with or corresponding to gene RIEG1;

Townes-Brocks syndrome, associated with or corresponding to gene SALL1;

Holoprosencephaly syndrome, associated with or corresponding to gene SHH;

Campomelic syndrome, associated with or corresponding to gene SOX9;

Hirschsprung syndrome, associated with or corresponding to gene SOX10;

Ulnar-mammary syndrome, associated with or corresponding to gene TBX3;

Holt-Oram syndrome, associated with or corresponding to gene TBS;

Treacher Collins syndrome, associated with or corresponding to gene TCOF1;

Denys-Drash syndrome, associated with or corresponding to gene WT1; or

Smith-Lemli-Opitz syndrome, associated with or corresponding to gene 7-DHCR.

Optionally, pharmaco-genomic mutation or bioinformatic value is indicated, determined, or generated, in part, to describe or suggest one or more cancer disease, disorder, or risk associated with tumor suppressor gene, such as:

Retinoblastoma, osteosarcoma, associated with or corresponding to gene RB1 (related p107, p130) at chromosome location 13q14;

Familial adenomatous polyposis, associated with or corresponding to gene APC at chromosome location 5q21;

Neurofibromatosis type 1, associated with or corresponding to gene NF1 at chromosome location 17q11;

Neurofibromatosis type 2, associated with or corresponding to gene NF2 at chromosome location 22q12;

Li-Fraumeni syndrome, associated with or corresponding to gene p53 (related p63, p73) at chromosome location 17p13;

Von Hippel-Lindau disease (renal cancer), associated with or corresponding to gene VHL at chromosome location 3p25;

Wilms tumor, associated with or corresponding to gene WT1 at chromosome location 11p13;

Familial melanoma, associated with or corresponding to gene p16 (related p15) at chromosome location 9p21;

Familial breast/ovarian cancer, associated with or corresponding to gene BRCA1 at chromosome location 17q21;

Familial breast cancer, associated with or corresponding to gene BRCA2 at chromosome location 13q12;

Cowden disease (breast and thyroid cancer), associated with or corresponding to gene PTEN at chromosome location 10q23;

Ataxia telangiectasia, associated with or corresponding to gene AT at chromosome location 11q22; or Li-Fraumeni syndrome, associated with or corresponding to gene CHK2 at chromosome location 22q12.

Optionally, pharmaco-genomic mutation or bioinformatic value is indicated, determined, or generated, in part, to describe or suggest one or more cancer disease, disorder, or risk associated with oncogene, such as:

Growth Factors:

Stomach carcinoma, associated with or corresponding to oncogene HST at chromosome location 11q13;

Glioma (brain tumor), associated with or corresponding to oncogene SIS at chromosome location 22q12;

Growth Factor Receptors:

Multiple endocrine neoplasia, associated with or corresponding to oncogene RET at chromosome location 10q;

Glioboastoma (brain tumor), breast cancer, associated with or corresponding to oncogene erb-B at chromosome location 10q;

Promyelocytic leukemia, associated with or corresponding to oncogene erb-A at chromosome location 17q11;

Neuroblastoma, associated with or corresponding to oncogene NEU at chromosome location 17q11;

Signal Transduction Proteins:

Carcinoma of colon, lung, pancreas, associated with or corresponding to oncogene H-RAS at chromosome location 11p15;

Melanoma, thyroid carcinoma, AML, associated with or corresponding to oncogene K-RAS at chromosome location 12p12;

Chronic myelogenous leukemia, acute lymphocytic leukemia, associated with or corresponding to oncogene Abl at chromosome location 9q34;

Transcription Factors:

Neuroblastoma, lung carcinoma, associated with or corresponding to oncogene N-myc at chromosome location 2p24;

Malignant melanoma, lymphoma, leukemia, associated with or corresponding to oncogene MYB at chromosome location 6q22; or Osteosarcoma, associated with or corresponding to oncogene Fos at chromosome location 14q24.

Optionally, pharmaco-genomic mutation or bioinformatic value is indicated, determined, or generated, in part, to describe or suggest one or more coronary heart disease or disorder or risk associated with lipoprotein gene, such as:

Apolipoprotein A-I at chromosome location 11q;
Apolipoprotein A-IV at chromosome location 11q;
Apolipoprotein C-III at chromosome location 11q;
Apolipoprotein B at chromosome location 2p;
Apolipoprotein C-I at chromosome location 19q;
Apolipoprotein C-II at chromosome location 19q;
Apolipoprotein E at chromosome location 19q
Apolipoprotein A-II at chromosome location 1p;
LDL receptor at chromosome location 19p;
Lipoprotein(a) at chromosome location 6q;
Lipoprotein lipase at chromosome location 8p;
Hepatic triglyceride lipase at chromosome location 15q;
LCAT at chromosome location 16q; or
Cholesterol ester transfer protein at chromosome location 16q.

Optionally, pharmaco-genomic mutation or bioinformatic value is indicated, determined, or generated, in part, to describe or suggest one or more inborn errors of metabolism disease, disorder, or risk associated with enzyme, such as:

Disorders of Amino Acid/Organic Acid Metabolism:
  Maple syrup urine disease, associated with or corresponding to enzyme branched-chain ketoacid decarboxylase;
  Methylmalonic academia, associated with or corresponding to enzyme methylmalonic CoA mutase;
  Multiple carboxylase deficiency, associated with or corresponding to enzyme biotin responsive carboxylase;
Disorders of Carbohydrate Metabolism:
  Glycogen storage disease, type 2, associated with or corresponding to enzyme α-Glucosidase;
  Galactosemia, associated with or corresponding to enzyme galactose-1-uridyl transferase;
Disorders of Lysosomal Enzymes:
  Gangliosidosis (all types), associated with or corresponding to enzyme β-Galactosidase;
  Mucopolysaccharidosis (all types), associated with or corresponding to disease-specific enzyme;
  Tay-Sachs disease, associated with or corresponding to enzyme hexosaminidase A;
Disorder of Purine and Pyrimidine Metabolism:
  Lesch-Nyhan syndrome, associated with or corresponding to enzyme hypoxanthine-guanine phosphoribosyl transferase; or
Disorder of Peroxisomal Metabolism:
  Zellweger syndrome, associated with or corresponding to enzyme long-chain fatty acids.

In clinical, managed-care, hospital, diagnostic, therapeutic, or biomedical application or embodiment, electronic label processor 40, using one or more firmware, source or object code software, configurable logic chip or device, digital signal processor, systolic processing array, or other finite state machine, actually or effectively compares set of bioinformatic values, preferably associated with same or different temporal states, to determine or otherwise recognize one or more pharmaco-genomic mutation associated with or corresponding to target patient, animal, plant, or other biological host.

Furthermore, label apparatus 40 may operate autonomously, in cooperation with other computer system nodes, clients, or processing elements, to collect, process and display various host or patient bioinformatic and non-bioinformatic information. For example, patient information and other personal or medical record data may be received via questionnaire or otherwise retrieved, such as host identification, drug treatment, prescription, and dosage, single or multiple concomitant food or drug allergy, interaction or side effect, pregnancy, lactation, as well as bioinformatic, genetic, proteomic, metabolomic, and other monitored or sensed mutation-related data as described herein.

Label apparatus 40 may be used in time-critical emergency, urgent, or trauma situation to improve patient healthcare diagnosis and treatment, for example, by early-detection, expediting and assisting physician, paramedical, nursing, or other professional analysis and treatment. Sensed or measured bioinformatic value as electronically labeled for indicating pharmaco-genomic mutation information, as described herein, significantly improves quality and accuracy of medication delivery and administration to identified subgroups of patients having certain adverse response to medication, food, or other treatment.

Additionally, such data may include pharmaco-genomic or pharmaco-kinetic clinical or indications based on genetic, proteomic, metabolomic (i.e., analysis of small organic cell molecules and metabolic response thereof), or other bioinformatic variant or mutation, or other genetic-based condition or profile (e.g., sex, race/ethnicity, etc.) such as drugs to be avoided, or considered as alternative. Thus optimally, host susceptibility or predisposition to toxicity or other adverse host reaction or side effects to certain identified food, drugs, or other medical treatment may be minimized, mitigated, or eliminated using automated rule-based advise or expert system.

For example, label apparatus 40 may alert medical professionals when host patient is determined via sense approach to detect pharmaco-genomic mutation described herein that patient ability to produce thiopurine S-methyltransferase (TPMT) enzyme activity is compromised. Here, TPMT genetic test (commercially available from DNA Sciences (Raleigh, N.C.) enables identification of patient at risk for 6-MP/azathioprine/thioguanine toxicity, and improves confidence through tailored dosing regimens, while minimizing concern over drug-induced complication.

Alternatively, pharmaco-genomic mutation to G protein-coupled receptors (GPCR) molecular target and variant alleles may be detected to electronically label and thereby effectively modify host drug therapy. Another pharmaco-genomic mutation that may be detected and labeled is enzyme debrisoquine hydroxylase (CYP2D6), isozyme of microsomal cytochrome P450 monooxygenase system; encoding gene is located in CYP2D gene cluster in contiguous 45-kb region of chromosome 22. Here, at least nine polymorphisms of CYP2D6 affect metabolism of more than 30 different pharmaceuticals, including β-adrenergic receptor antagonists, neuroleptics, and tricyclic antidepressants.

Label display 48 visually or audibly indicates to doctor, nurse, or other medical or technical staff textual, symbolic or graphic representation of one or more detected pharmaco-genomic mutation. Such indication may be network-accessible for modified medical message.

Label apparatus 40 may couple electronically or digitally to hospital, physician, nursing, and other medical staff communication system to enable network-accessible prescription renewal, appointment scheduling, lab-result entry and retrieval, referrals to specialists and disease management, as well as generally computerized physician or pharmacy-ordering scheme, patient communications, access to bioinformatic test or sensor results, insurance claim status, and bar-coding of pharmaceuticals, and automated medication checks for possible errors, preferably in accordance with pharmaco-genomic labeling approach described herein.

Compare method or genetic algorithm may employ simple identical or substantial equivalent value check between recently-measured value and previously-stored value for same host, for example, after host exposure to radiation or other carcinogenic sources. Such algorithm may be executed to adapt iteratively or dynamically in real-time or in multiple or parallel processors based on currently or recently-measured, monitored, or sensed host bioinformatic values, for example using fuzzy system, Bayesian or neural network, to improve compute or processing performance by comparing initially values that previously are known or recorded to be related or likely to be related or otherwise weighted to pharmaco-genomic mutation.

Additionally, electronic access to bioinformatic value or pharmaco-genomic mutation information may be restricted, secured, encrypted, or excluded unless the host thereof explicitly or voluntarily provides prior informed consent to access such information.

Hence, comparison serves to detect presence or absence of bioinformatic value (e.g., oncogene, tumor suppressor gene, allele, enzyme, repeat sequence, micro-deletion, or other mutant gene product, protein, or metabolome) that causes, or increases or decreases risk of one or more host disease, disorder, syndrome, allergy, or other biological condition.

Such bioinformatic value or pharmaco-genomic mutation information may be stored in label memory 44 or in other digital storage accessible or otherwise retrievable through network 50. Such stored information may be formatted according to one or more conventional, industry-standard, or otherwise publicly or commercially-available software, processing, storage, and communications protocol, as well as databases for metabolic, signaling, regulatory and pathway data.

Additionally, as appropriate, other genomic relational or object-oriented knowledge base or data sources may be network-accessed, such as GenBank, Unigene, LocusLink, Homologene, Ensemble, GoldenPath, or NCICB Cancer Genome Anatomy Project (CGAP). Such information may be accessed using ontology-based interfaces that are defined to be logically related, for example, using annotation format such as Distributed Annotation System (DAS).

Optionally, bioinformatic value-related function or clinical step may be specified and otherwise annotated, such as hypothesis definition, experiment design, sample preparation and distribution, experiment run, data acquisition, result analysis, data mining, design refinement, modeling, knowledge discovery, or project report.

Additionally, such functions may be applied to bioinformatic data processed by software or hardware analysis tools for pharmacogenomics, gene expression, high-throughput sequencing, or proteomics (functional or structural) use-case domains.

Preferably such stored information complies, at least in part, with data exchange and management framework and specifications provided by Interoperable Informatics Infrastructure Consortium (I3C), which technical and use-case model documents, and recommended implementations, as described on-line at http://www.i3c.org/ are hereby incorporated by reference as appropriate herein.

For example, one or more I3C-compliant or recommended data format may be employed during operation of electronic label processor, as described herein. Accordingly bioinformatic values may be accessed, and displayed or otherwise imaged using electronic display I/O 48 hardware or software, for gel chromatography images, original data from biological arrays, arrays of time-series data from mass spectrometry, illustrative functional depiction of proteins, simple microscope images, patient records with medical images, derived data from multiple or time-series images, electrocardiograms, or original drawings and annotations to medical images made by examining professionals. On-screen search capability enables medical professional quickly to locate and interpret particular host bioinformatic data, such as gene sequence, protein, enzyme, allele, or other related detail.

Additionally, I3C-compliant or recommended data format may be employed to provide clinical trial FDA pharmacogenomic submission data, including genotype, haplotype, phenotype, or derived analysis format; and pathways and system biology information for data, models and simulations, for example of networks and pathways based on pair-wise labeled relationships between proteins, genes, and RNA transcripts, as well as virtual cell systems. For example, design synthesis, test, and simulation of virtual cell system biology enables perturbation or mutagenesis stimulation to predict behavior according to host drug metabolism, transport, distribution, or excretion.

Network 50 access to various databases or other digital repository may couple in n-tiered architecture multiple client interfaces, serve components, back-end objects and data sources. For example, Netscape or Microsoft Internet Explorer browsers or applications, e.g., based on Java, non-Java, Perl, C, C++, or other programming or development software, run on client nodes 60 may receive information, such as in various markup-language, e.g., HTML, XML, etc., from back-end objects over conventional network messaging or transport protocol, e.g., hyper text transfer protocol (HTTP), TCP Internet Protocol, simple object access protocol (SOAP), file transfer protocol (FTP), HOP, etc. Additionally, Universal Description Discovery Integration (UDDI) registry and Resource Description Framework (RDF) agent advertising formats may be used.

As described herein, pharmaco-genomic mutation data may be generated and displayed by label apparatus 40. Genomic, proteomic, or metabolomic sequence analysis software tool, for example, (e.g., BLAST, TimeLogic) may be used by controller 42 to discover or characterize host genomic, proteomic, or metabolomic sequence, acquired and qualified from one or more sources, such as sensor 49 or database 44. Thus, internal and external sequence and protein libraries may be updated and maintained, certain redundant, unqualified or external data being filtered for internal sequence processing. One or more target, putative or otherwise mutant gene or bioinformatic value is then determined and cataloged effectively by label apparatus 40.

Optionally, hypothetical function of such determined gene or value may then be generated manually, automatically, or homologously by finding similarity to known or other prior values. Genetic, proteomic, or metabolomic analysis protocols and similarity analysis may be defined and selected, thereby enabling or constructing functional hypotheses to be generated, prioritized, or reviewed using sensor measurements or other host evidence.

Proteolysis sample preparation may be performed (e.g., HPLC, gel electrophoresis), then mass spectroscopy or tandem MS analysis and compression, quantitization, and fragment size genome analysis for candidate prediction, proteome or metabolome comparison, and other quantitative analysis using modeling tools and databases.

The foregoing descriptions of specific embodiments of the invention have been presented for purposes of illustration and description. They are not intended to be exhaustive or to limit the invention to the precise forms disclosed. Obviously, many modifications and variations are possible in light of the above teaching, including pharmaco-genomic mutation labeling to alert potential or actual medical associated risk with organ transplant, paternity identification, genetically-modified agricultural crops, antisense and gene vaccine or therapy. The embodiments were chosen and described in order to explain the principles and the application of the invention, thereby enabling others skilled in the art to utilize the invention in its various embodiments and modifications according to the particular purpose contemplated. The scope of the invention is intended to be defined by the claims appended hereto and their equivalents.

What is claimed is:

1. A mobile hand-held wireless sensor-based electronic system for displaying a comparison of a first bioinformatic value and a second bioinformatic value to detect GPCR pharmaco-genomic mutation, the system comprising:
   a processor,
   a display,
   and a storage;
      wherein said processor is coupled to the display and displays said comparison,
      wherein said comparison uses said processor to determine a pharmaco-genomic mutation associated with a host, said comparison and associated pharmaco-genomic mutation being stored in the storage, and wherein said processor is effective to access said comparison and associated pharmaco-genomic mutation from storage and indicate said pharmaco-genomic mutation on said display,
      wherein said pharmaco-genomic mutation is determined electronically by the processor automatically analyzing said compared bioinformatic values to detect G protein-coupled receptors (GPCR) molecular target and variant alleles,
      wherein the processor, display and storage functionally embody an electronic medical label using a rule-based advisor expert system that electronically generates an audio-visual alert comprising a genetic mutation and pharmaco-kinetic clinical indication to one or more time-critical or urgent-care medical professional, said rule-based advisor expert system determining one or more patient pharmaco-genomic profile according to the compared bioinformatic values associated with the host to generate further via the audio-visual alert including one or more monitored risk and appropriate medication associated with the detected GPCR molecular target and variant alleles, thereby optimally expediting GPCR-related medication using the electronic medical label according to the rule-based advisor expert system automated analysis of one or more host susceptibility or predisposition to pharmaco-genomic or pharmaco-kinetic toxicity or other adverse host reaction or side effects to one or more food, drug or treatment;
   wherein the processor, display and storage are embodied functionally in a mobile hand-held system further comprising a sensor integrated therewith that is wirelessly accessible via a wireless communication network, such sensor sensing GPCR molecular target and variant alleles using integrated chip refractive-index micro-interferometry detection using coherent VCSEL, laser diode, or He—Ne laser source, etched substrate capillary channel for sample reception and analysis, and reflected laser-light reflection photodetector, and the sensor further senses GPCR molecular target and variant alleles using an affinity-based biosensor based on optical evanescent wave detector using flow-based surface plasmon resonance in micro-fabricated integrated fluidic cartridge to capture tagged proteins, thiol coupling, or coil-coil interaction, wherein resonance angle is continuously monitored to detect changes in refractive resonance angle and refractive index corresponding to changes in mass when certain ligand binds to, or dissociates from, immobilized binding partner;
   wherein said processor that determines the pharmaco-genomic mutation and rule-based advisor expert system comprises one or more systolic array-based fuzzy logic and Bayesian or neural network-implemented virtual cell systems biology software that models and simulates perturbation and mutagenesis stimulation to predict GPCR pharmaco-genomic mutation behavior according to host drug metabolism, transport, distribution and excretion automatically using sensed GPCR molecular target and variant alleles using the affinity-based biosensor having the optical evanescent wave detector and integrated chip refractive-index micro-interferometry detection based on pair-wise labeled relationships between proteins, genes and RNA transcripts further detected by said processor that determines the pharmaco-genomic mutation and rule-based advisor expert system using semiconductor nanocrystal or quantum-dot device that links or bonds to one or more affinity molecules of an analyte comprising sensed GPCR molecular target and variant alleles, whereupon such nanocrystal probe in response to a first energy associated with a presence of sensed GPCR molecular target and variant alleles excites the nanocrystal or quantum-dot device causing such probe to provide a second energy or generate or fluoresce a distinct wavelength signal indicating GPCR pharmaco-genomic mutation to alert potential or actual medical associated risk with organ transplant, paternity identification, genetically-modified agricultural crops, antisense and gene vaccine or therapy;
   wherein said processor comprises the one or more systolic array that models and simulates perturbation and mutagenesis stimulation to predict GPCR pharmaco-genomic mutation behavior according to host drug metabolism, transport, distribution and excretion using sensed GPCR molecular target and variant alleles predictably to alert potential or actual medical associated risk with organ transplant, paternity identification, genetically-modified agricultural crops, antisense, and gene vaccine or therapy based on pair-wise labeled relationships between proteins, genes and RNA transcripts further detected by said processor when determining the pharmaco-genomic mutation using the semiconductor nanocrystal or quantum-dot device that links or bonds to one or more affinity molecules of an analyte comprising sensed GPCR molecular target and variant alleles, whereupon such nanocrystal probe in response to first energy associated with a presence of sensed GPCR molecular target and variant alleles excites the nanocrystal or quantum-dot device causing such probe to provide second energy or generate or fluoresce a distinct wavelength signal indicating GPCR pharmaco-genomic mutation, thereby automatically enabling the one or more systolic array to alert potential or actual medical associated risk with organ transplant, paternity identification, genetically-modified agricultural crops, antisense, and gene vaccine or therapy based on pair-wise labeled relationships between proteins, genes and RNA transcripts to predict GPCR pharmaco-genomic mutation behavior according to host drug metabolism, transport, distribution and excretion using sensed GPCR molecular target and variant alleles.

2. The system of claim 1 wherein:
said processor communicates with the system through a network interface, the system being configured to access the storage through the interface.

3. The system of claim 1 wherein:
said pharmaco-genomic mutation is effective to indicate a medical message and said processor displays a modified medical message.

4. The system of claim 1:
further comprising a means for storing and comparing a third bioinformatic value and a fourth bioinformatic value to determine an additional pharmaco-genomic mutation associated with a different host, said processor being coupled to another system,
wherein the other system comprises a means for indicating the pharmaco-genomic mutation associated with said different host, the processor accesses the comparison and associated additional pharmaco-genomic mutation from the storage.

5. The system of claim 1 wherein:
said processor determines the first and second bioinformatic values at different times.

6. A mobile hand-held wireless sensor-based electronic method for displaying a pharmaco-genomic mutation associated with GPCR, the method comprising steps:
comparing by a processor a first bioinformatic value and a second bioinformatic value to determine a pharmaco-genomic mutation; and
displaying by the processor a determination of the pharmaco-genomic mutation,
wherein the processor automatically analyzes said compared bioinformatic values to detect G protein-coupled receptors (GPCR) molecular target and variant alleles,
wherein the processor functionally embodies an electronic medical label using a rule-based advisor expert system that electronically generates an audio-visual alert comprising a genetic mutation and pharmaco-kinetic clinical indication to one or more time-critical or urgent-care medical professional, said rule-based advisor expert system determining one or more patient pharmaco-genomic profile according to the compared bioinformatic values associated with the host to generate further via the audio-visual alert including one or more monitored risk and appropriate medication associated with the detected GPCR molecular target and variant alleles, thereby optimally expediting GPCR-related medication using the electronic medical label according to the rule-based advisor expert system automated analysis of one or more host susceptibility or predisposition to pharmaco-genomic or pharmaco-kinetic toxicity or other adverse host reaction or side effects to one or more food, drug or treatment;
wherein the processor, display and storage are embodied functionally in a mobile hand-held system further comprising a sensor integrated therewith that is wirelessly accessible via a wireless communication network, such sensor sensing GPCR molecular target and variant alleles using integrated chip refractive-index micro-interferometry detection using coherent VCSEL, laser diode, or He—Ne laser source, etched substrate capillary channel for sample reception and analysis, and reflected laser-light reflection photodetector, and the sensor further senses GPCR molecular target and variant alleles using an affinity-based biosensor based on optical evanescent wave detector using flow-based surface plasmon resonance in micro-fabricated integrated fluidic cartridge to capture tagged proteins, thiol coupling, or coil-coil interaction, wherein resonance angle is continuously monitored to detect changes in refractive resonance angle and refractive index corresponding to changes in mass when certain ligand binds to, or dissociates from, immobilized binding partner;
wherein said processor that determines the pharmaco-genomic mutation and rule-based advisor expert system comprises one or more systolic array-based fuzzy logic and Bayesian or neural network-implemented virtual cell systems biology software that models and simulates perturbation and mutagenesis stimulation to predict GPCR pharmaco-genomic mutation behavior according to host drug metabolism, transport, distribution and excretion automatically using sensed GPCR molecular target and variant alleles using the affinity-based biosensor having the optical evanescent wave detector and integrated chip refractive-index micro-interferometry detection based on pair-wise labeled relationships between proteins, genes and RNA transcripts further detected by said processor that determines the pharmaco-genomic mutation and rule-based advisor expert system using semiconductor nanocrystal or quantum-dot device that links or bonds to one or more affinity molecules of an analyte comprising sensed GPCR molecular target and variant alleles, whereupon such nanocrystal probe in response to a first energy associated with a presence of sensed GPCR molecular target and variant alleles excites the nanocrystal or quantum-dot device causing such probe to provide a second energy or generate or fluoresce a distinct wavelength signal indicating GPCR pharmaco-genomic mutation to alert potential or actual medical associated risk with organ transplant, paternity identification, genetically-modified agricultural crops, antisense and gene vaccine or therapy;
wherein said processor comprises the one or more systolic array that models and simulates perturbation and mutagenesis stimulation to predict GPCR pharmaco-genomic mutation behavior according to host drug metabolism, transport, distribution and excretion using sensed GPCR molecular target and variant alleles predictably to alert potential or actual medical associated risk with organ transplant, paternity identification, genetically-modified agricultural crops, antisense, and gene vaccine or therapy based on pair-wise labeled relationships between proteins, genes and RNA transcripts further detected by said processor when determining the pharmaco-genomic mutation using the semiconductor nanocrystal or quantum-dot device that links or bonds to one or more affinity molecules of an analyte comprising sensed GPCR molecular target and variant alleles, whereupon such nanocrystal probe in response to first energy associated with a presence of sensed GPCR molecular target and variant alleles excites the nanocrystal or quantum-dot device causing such probe to provide second energy or generate or fluoresce a distinct wavelength signal indicating GPCR pharmaco-genomic mutation, thereby automatically enabling the one or more systolic array to alert potential or actual medical associated risk with organ transplant, paternity identification, genetically-modified agricultural crops, antisense, and gene vaccine or therapy based on pair-wise labeled relationships between proteins, genes and RNA transcripts to predict GPCR pharmaco-genomic mutation behavior according to host drug metabolism, transport, distribution and excretion using sensed GPCR molecular target and variant alleles.

7. The method of claim 6 wherein:
said processor communicates with the system through a network interface, the system being configured to access the storage through the interface.

8. The method of claim 6 wherein:
said pharmaco-genomic mutation is effective to indicate a medical message and said processor displays a modified medical message.

9. The method of claim 6:
further comprising storing and comparing a third bioinformatic value and a fourth bioinformatic value to determine an additional pharmaco-genomic mutation associated with a different host, said processor being coupled to another system,
wherein the other indicates the pharmaco-genomic mutation associated with said different host, the processor accesses the comparison and associated additional pharmaco-genomic mutation from the storage.

10. The method of claim 6 wherein:
said processor determines the first and second bioinformatic values at different times.

* * * * *